(12) United States Patent
Huczynski et al.

(10) Patent No.: US 12,741,974 B2
(45) Date of Patent: Sep. 22, 2026

(54) COMPOUNDS CONSTITUTING C20-MODIFIED SALINOMYCIN DERIVATIVES, A METHOD FOR OBTAINING THE SAME, A COMPOSITION CONTAINING THE SAME, A USE OF SAID COMPOUNDS AND A METHOD FOR OBTAINING AN INTERMEDIATE PRODUCT

(71) Applicant: FILECLO SP. Z O.O., Lodz (PL)

(72) Inventors: Adam Huczynski, Poznan (PL); Michal Antoszczak, Biedrusko (PL)

(73) Assignee: FILECLO SP. Z O.O., Lodz (PL)

( * ) Notice: Subject to any disclaimer, the term of this patent is extended or adjusted under 35 U.S.C. 154(b) by 981 days.

(21) Appl. No.: 17/796,879

(22) PCT Filed: Feb. 5, 2021

(86) PCT No.: PCT/EP2021/052843

§ 371 (c)(1),
(2) Date: Aug. 2, 2022

(87) PCT Pub. No.: WO2021/156461

PCT Pub. Date: Aug. 12, 2021

(65) Prior Publication Data

US 2022/0402932 A1 Dec. 22, 2022

(30) Foreign Application Priority Data

Feb. 7, 2020 (PL) ........................................ 432858

(51) Int. Cl.
*C07D 493/20* (2006.01)
*A61P 35/00* (2006.01)
*C07D 493/10* (2006.01)

(52) U.S. Cl.
CPC ............ *C07D 493/20* (2013.01); *A61P 35/00* (2018.01); *C07D 493/10* (2013.01)

(58) Field of Classification Search
None
See application file for complete search history.

(56) References Cited

U.S. PATENT DOCUMENTS

| | | | | |
|---|---|---|---|---|
| 10,287,298 | B2 * | 5/2019 | Mehrpour | A61P 33/06 |
| 2024/0294541 | A1 * | 9/2024 | Czerwonka | A61K 31/422 |
| 2024/0400576 | A1 * | 12/2024 | Rodriguez | A61P 35/00 |
| 2025/0250280 | A1 * | 8/2025 | Rodriguez | C07D 493/20 |

FOREIGN PATENT DOCUMENTS

| | | | |
|---|---|---|---|
| EP | 3191493 | A1 | 7/2017 |
| WO | 2013103993 | A1 | 7/2013 |

OTHER PUBLICATIONS

Li et al., Eur J Med Chem. Mar. 25, 2018;148:279-290 (Year: 2018).*

Li Yu et al: "Synthesis and biological evaluation of 20-epi-amino-20-deoxysalinomycin derivatives", European Journal of Medicinal Chemistry, vol. 148, Mar. 1, 2018 (Mar. 1, 2018), pp. 278-290, XP055788796, Amsterdam, NL ISSN: 0223-5234, DOI: 10.1016/j.ejmech.2018.02.004.

* cited by examiner

*Primary Examiner* — Jeffrey S Lundgren
*Assistant Examiner* — Anthony Joseph Seitz
(74) *Attorney, Agent, or Firm* — Finnegan, Henderson, Farabow, Garrett & Dunner, LLP

(57) ABSTRACT

The invention relates to compounds constituting C20-N-acyl derivatives of salinomycin with the general formula (2):

(2)

and their salts, where X denotes R, O—R or NH—R, and R is as defined in the claims and in the description. The invention also relates to a composition comprising the compound defined above and at least one pharmaceutically acceptable excipient. The invention also relates to a method for obtaining salinomycin derivatives with the general formula (2), as well as an intermediate product for obtaining these compounds. The invention also relates to compounds constituting C20-N-acyl derivatives of salinomycin with the general formula (2) for use as a medicament, particularly as anti-cancer agents.

12 Claims, No Drawings

COMPOUNDS CONSTITUTING C20-MODIFIED SALINOMYCIN DERIVATIVES, A METHOD FOR OBTAINING THE SAME, A COMPOSITION CONTAINING THE SAME, A USE OF SAID COMPOUNDS AND A METHOD FOR OBTAINING AN INTERMEDIATE PRODUCT

TECHNICAL FIELD

The invention relates to individually modified salinomycin derivatives modified at position C-20, a method for obtaining the same, a composition containing the same, and a use thereof as a medicament, particularly as an anti-cancer agent. The invention also relates to a method for obtaining an intermediate product in a method for obtaining salinomycin derivatives modified at position C-20.

BACKGROUND

One of the most utilized ways of identifying new cancer drugs is chemical modification of compounds of natural origin that have demonstrated high biological activity. Salinomycin is a natural polyether ionophore antibiotic isolated from *Streptomyces albus* commonly used in veterinary with the formula (1):

(1)

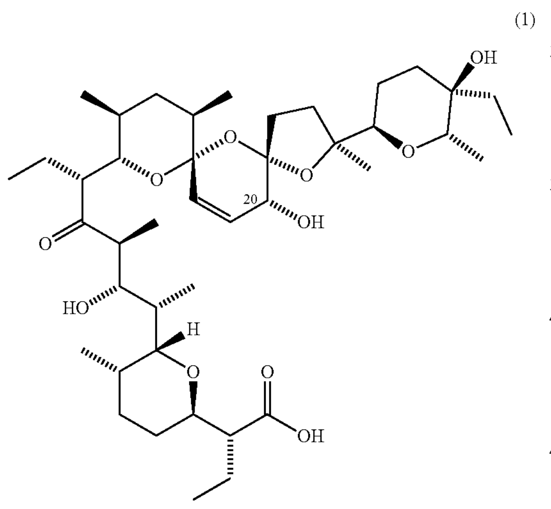

Salinomycin is known for its high anti-microbial activity, but also for its anti-cancer activity. In in vitro and in vivo tests, salinomycin has shown efficacy against a variety of cancer cells, including drug-resistant cells and cancer stem cells. The mechanism of biological action of salinomycin is related to the ability of this compound to selectively complex metal cations, primarily sodium and potassium cations, and to transport them subsequently across biological membranes. This leads to an imbalance of cations in the cell, changes in intracellular pH, and ultimately results in cell death. The high anti-cancer activity of salinomycin is also related to the effect of said compound on various molecular targets and signalling pathways, including AMPK, MAPK, VEGF or Wnt/β-catenin. Salinomycin has been successfully used on a small group of patients with advanced head, neck, breast and ovarian cancer. Salinomycin therapy resulted in inhibition of cancer progression with no acute side effects, thus demonstrating a high therapeutic potential of this compound.

Patent application EP3191493 and a scientific publication [Mai et al., *Nature Chemistry,* 9, 2017, 1025-1033] disclose amine derivatives of salinomycin obtained at C-20 position. In in vitro studies, some compounds exhibited higher anti-cancer activity and selectivity against CD24 cancer stem cells, as well as the ability to inhibit mammosphere formation compared to the original salinomycin. The use of amine derivatives of salinomycin at C-20 position also resulted in a reduction in the volume and weight of tumours in mice with implanted human MCF-7 breast cancer. The high anti-cancer activity of said derivatives is related to their ability to induce ferroptosis, i.e. programmed cell death dependent on iron cation content. The findings disclosed in patent application EP3191493 and the scientific publication [Mai et al., *Nature Chemistry,* 9, 2017, 1025-1033] refer only to in vivo studies conducted in mice. The body of a mouse differs significantly from that of the human, which makes it is impossible to simply translate the results of these studies into the real therapeutic potential of the salinomycin derivatives obtained.

Now, in the scientific publication [Li et al., *European Journal of Medicinal Chemistry,* 148, 2018, 279-290], the authors disclosed N-amide and N-carbamate (urethane) derivatives of C20-epi-salinomycin with an reversed absolute configuration (S instead of R absolute configuration) on the asymmetric carbon at the C-20 position. The in vitro anti-cancer activity of said compounds was tested against a series of cancer cell lines: 4T1 (murine mammary carcinoma), A549 (human lung adenocarcinoma), HL-60 (human promyelocytic leukaemia), HeLa (human cervical cancer), MCF-7 (human breast cancer), SMMC-7721 (human liver cancer) and SW480 (human colon adenocarcinoma). Data disclosed in a scientific publication [Li et al., *European Journal of Medicinal Chemistry,* 148, 2018, 279-290] demonstrate that most of the obtained C20-epi-salinomycin derivatives exhibit higher anti-cancer activity compared to the starting compound. Studies conducted on the normal BEAS-2B cell line (human bronchial epithelial cells) further revealed that the C20-epi-salinomycin with the highest anti-cancer activity are further characterised by high selectivity of action, which in some cases is several times higher than that exhibited by chemically non-modified salinomycin. The information disclosed in the scientific publication [Li et al., *European Journal of Medicinal Chemistry,* 148, 2018, 279-290] is limited to in vitro studies only, which means that the effect of said compounds "in the living body" (in vivo studies) remains unknown. The ability of the resulting C20-epi-salinomycin derivatives to overcome drug resistance of cancer cells is also unknown.

SUMMARY OF THE INVENTION

The anti-cancer activity of biologically active compounds, including salinomycin and derivatives thereof, is closely correlated to the type of cell lines used in the tests. None of the salinomycin derivatives synthesised so far, however, has found a practical medical application, which is due for example to low bioactivity, low selectivity of action, lack of detailed studies on the mechanisms of biological action or pharmacokinetic and pharmacodynamic properties.

This is why concentrated efforts are continued to obtain salinomycin derivatives with a high therapeutic index, which would be applicable in oncology therapy.

Obtaining new salinomycin derivatives involves a number of synthetic problems that need to be solved. Salinomycin and intermediate products required to obtained derivatives thereof may be unstable in the reaction medium, especially in the presence of acidic and/or basic agents. Salinomycin, as well as its derivatives, are sensitive to high temperatures and may therefore undergo irreversible degradation. The presence of multiple functional groups presents an additional challenge for selective modification of salinomycin molecule, including any chemo- and regioselective modification of one of the three hydroxyl groups present within its structure. Another problem is the exorbitant price of commercially available salinomycin, which significantly hinders the development of new and efficient methods for chemical modification of the compound.

Accordingly, the invention addresses prior art difficulties regarding the preparation of salinomycin derivatives modified at the C-20 position while retaining the absolute configuration R on the asymmetric C-20 carbon atom (as in the starting salinomycin). The subject matter of the invention was therefore to obtain new salinomycin derivatives modified at C-20 position using the method according to the invention. Said method comprises obtaining an intermediate product as a result of specific transformations involving selected reactions, reactants and agents as well as conditions of the reaction allowing said derivatives to be obtained while retaining the absolute configuration R at the asymmetric carbon at the C-20 position in a relatively uncomplicated and efficient process.

A further subject matter of the invention was to obtain new derivatives of the natural ionophore salinomycin, in acidic form and salts thereof, modified at the C-20 position, which could be used in anti-cancer therapy. It is also an subject matter of the invention to provide such salinomycin derivatives modified at the C-20 carbon having an activity against cancer cells with highly advantageous selectivity.

Surprisingly, it was found that the salinomycin derivatives according to the invention have very good activity and selectivity against neoplastic diseases, in particular against cancers selected from the group comprising: melanoma, colon cancer, breast cancer or biphenotypic leukaemia.

The invention relates to compounds constituting C20-N-acyl derivatives of salinomycin with the general formula (2):

(2)

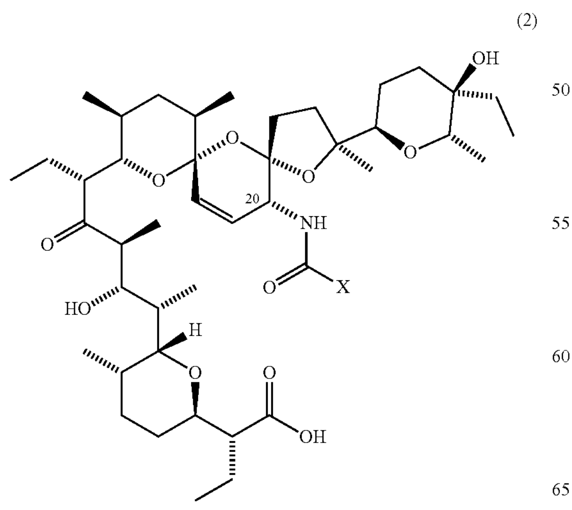

wherein:

X denotes R, O—R or NH—R;

R denotes:

- a straight-chain or branched-chain alkyl group comprising 1 to 10 carbons,
- a straight-chain or branched-chain alkyl group comprising 1 to 10 carbons which is substituted at any position of the carbon chain by 1 to 5 halogens, which may be present at the same carbon or at different carbons,
- a straight-chain alkyl group comprising 2 to 10 carbons which comprises ether moiety at any position of the carbon chain,
- a straight-chain alkyl group comprising 3 to 10 carbons which comprises multiple bonds, either double or triple bonds, at any position of the carbon chain,
- a monocyclic, dicyclic or tricyclic alkyl group comprising 5 to 10 carbons,
- an aromatic aryl group, wherein those comprising a six-membered aromatic ring are preferred,
- an aromatic aryl group substituted by 1 to 3 substituents independently selected from alkyl, alkoxy, hydroxy, nitro and nitrile groups or halogens,
- an aromatic heteroaryl group, wherein 1 or more carbons are substituted by 1 or more heteroatoms from a group comprising atoms of oxygen, nitrogen or sulphur, or
- an alkyl-aryl group, wherein the aromatic aryl group as defined above is linked to a salinomycin molecule by a carbon chain comprising 1 to 5 carbons (alkyl comprising 1-5 carbons);

as well as to salts thereof.

Preferably, these compounds are derivatives with the following formulae:

(9)

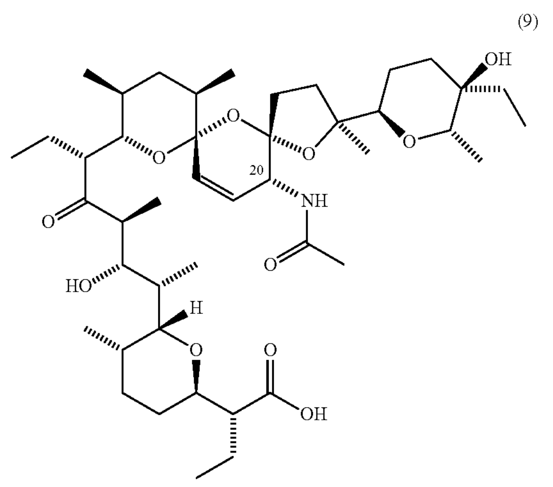

-continued
(10)
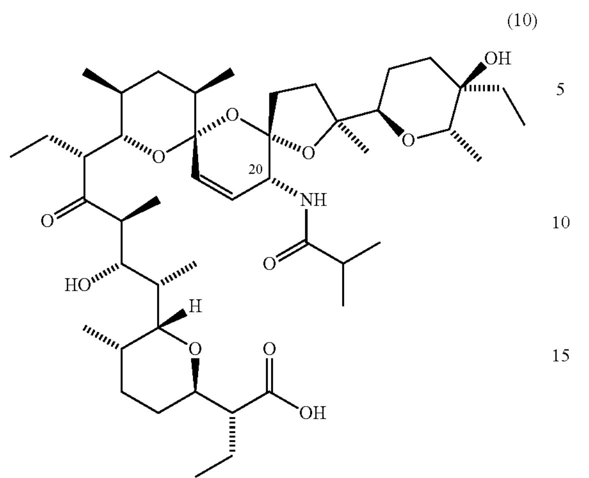
(11)
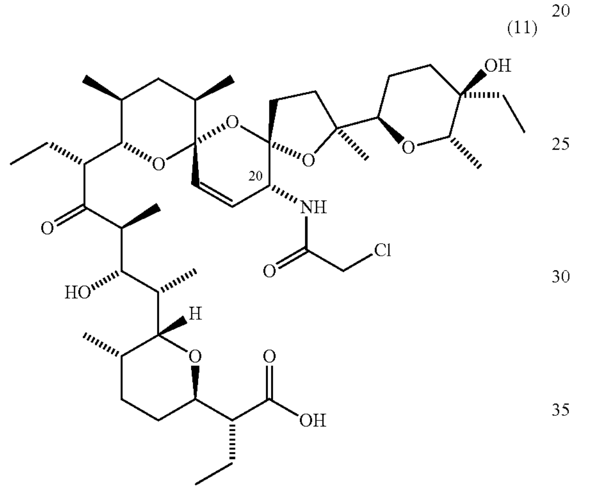
(12)
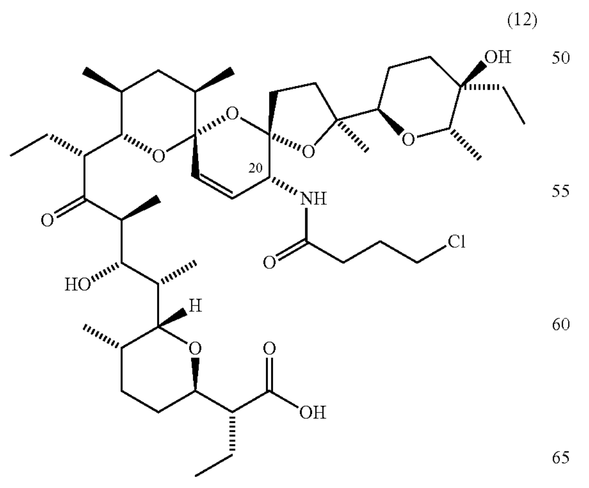
-continued
(13)
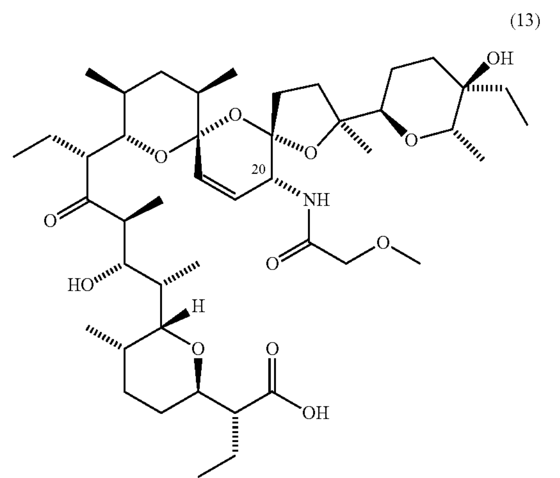
(14)
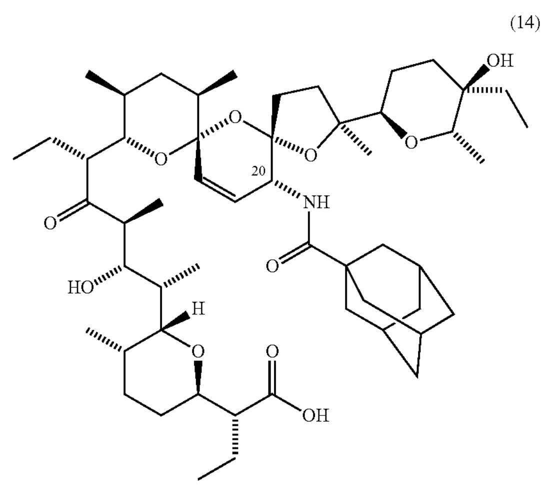
(15)
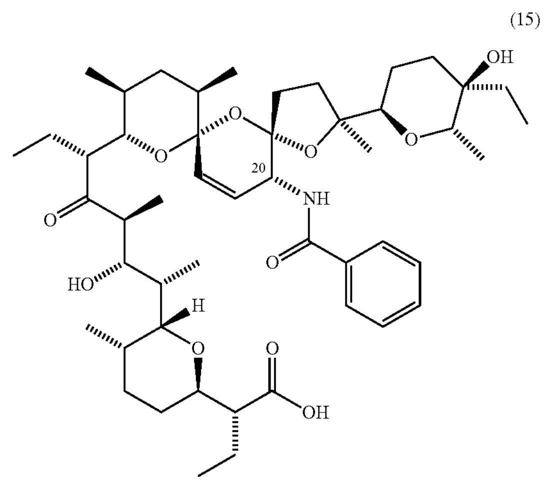

-continued
(16)
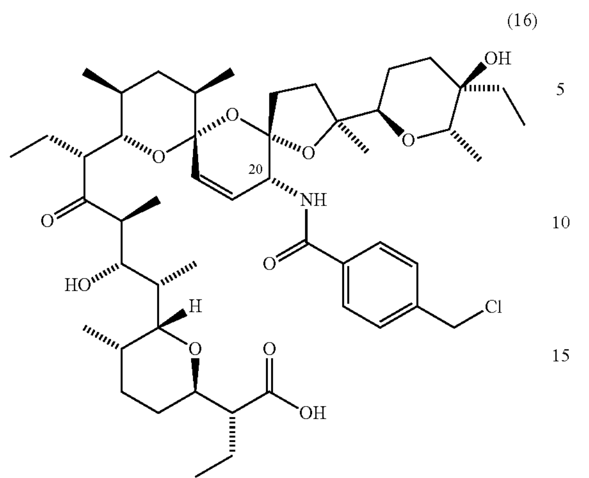
(17)
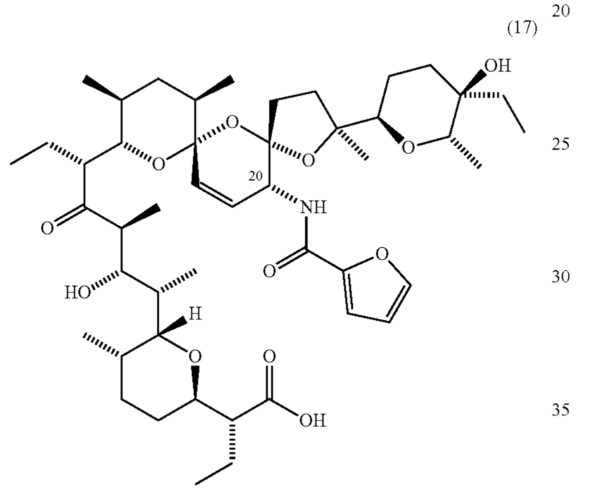
(18)
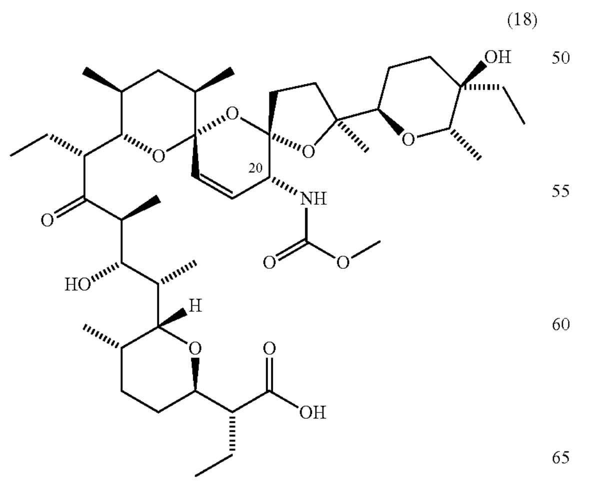
-continued
(19)
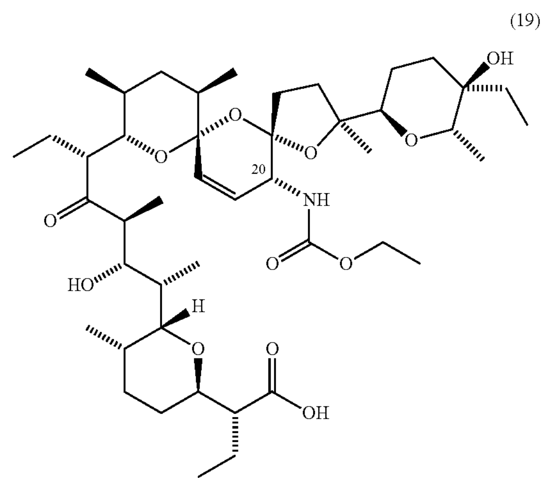
(20)
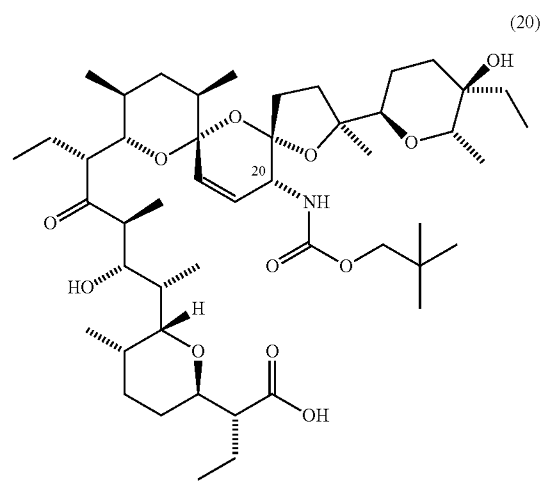
(21)
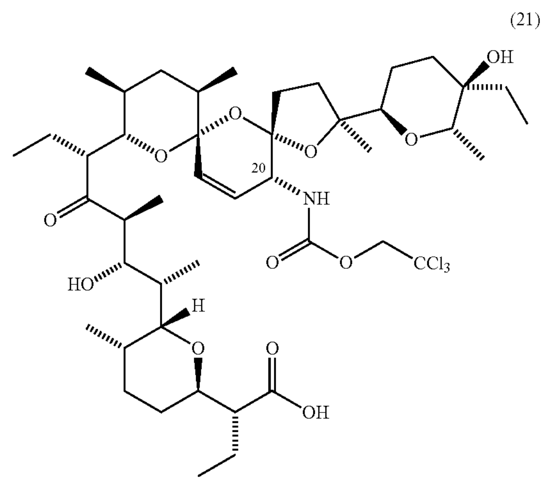

-continued
(22)
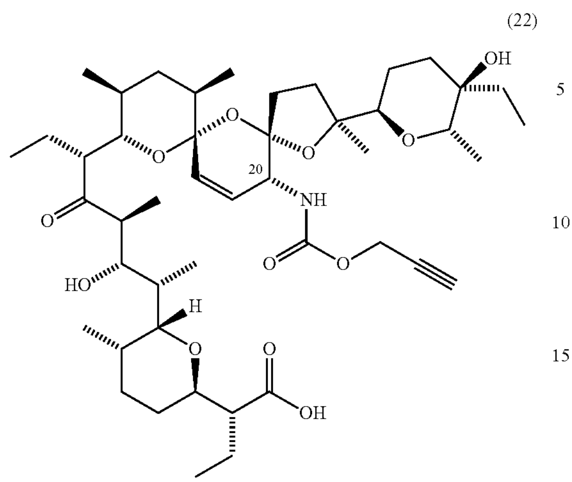
(23)
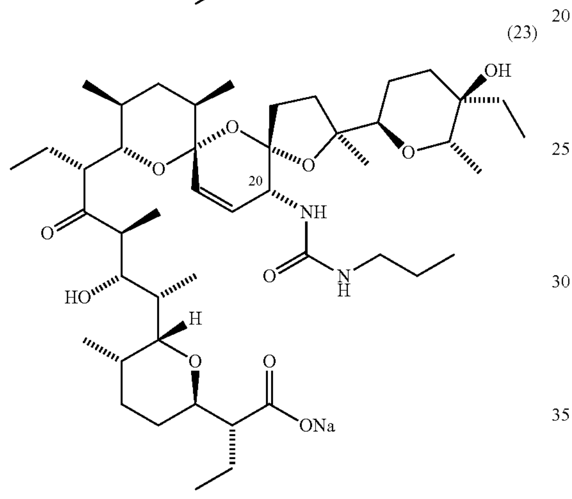
(24)
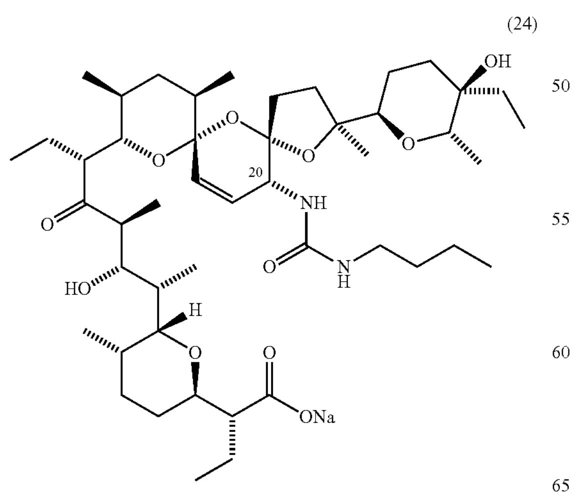
-continued
(25)
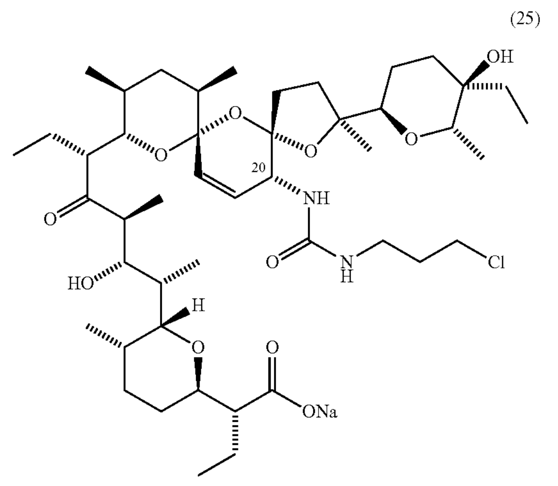
More preferably, the inventive compounds have the following formulae:
(10)
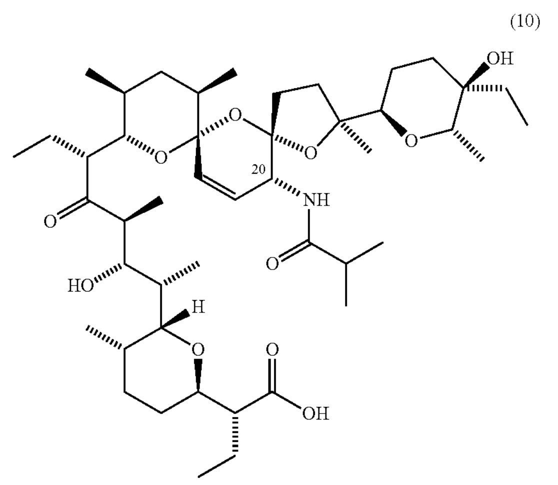
(12)
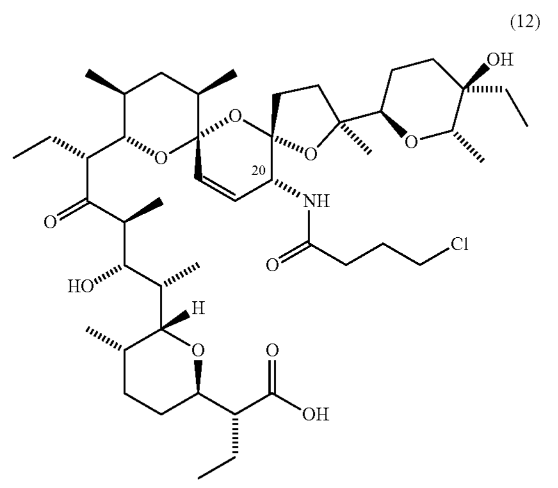

(13)
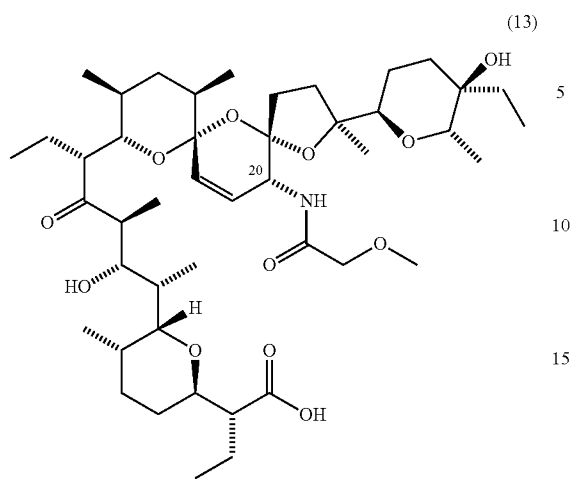
(21)
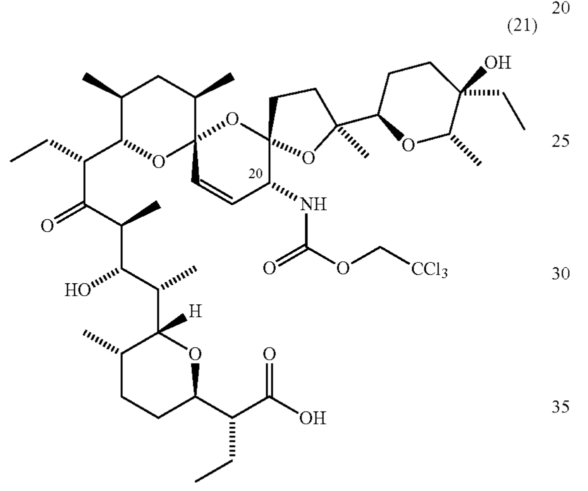
(22)
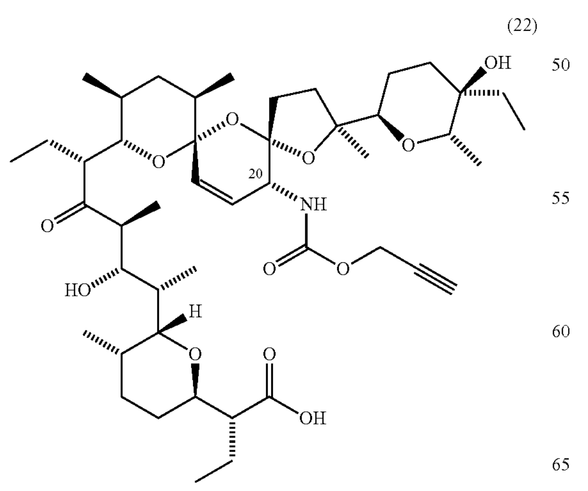
(23)
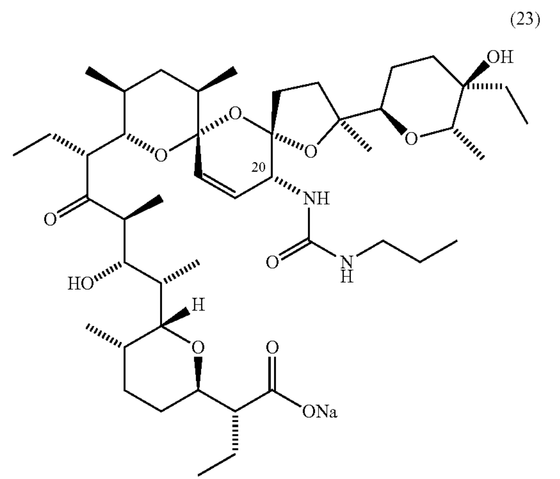
(25)
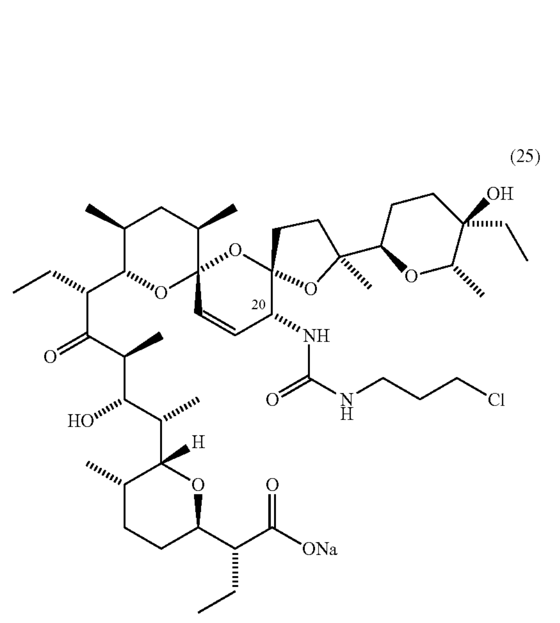
Preferably, the compound has the following formula:
(21)
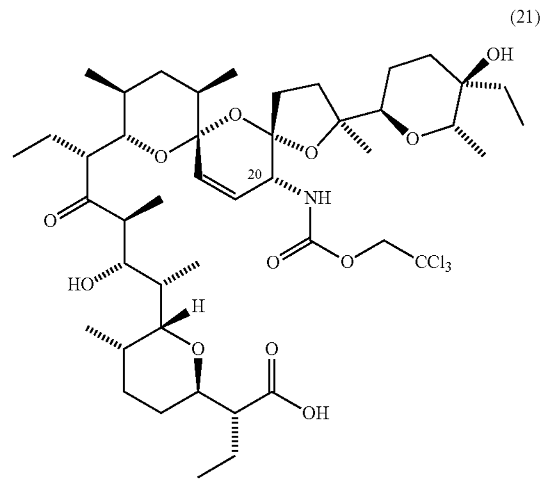

Also preferably, the compound has the following formula:

(25)

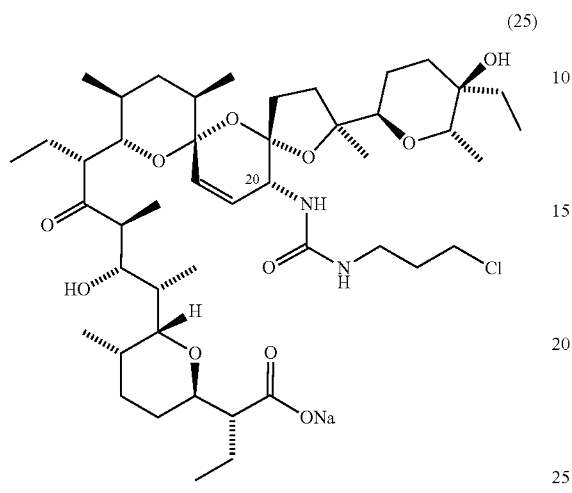

The invention also relates to a pharmaceutical composition comprising the compound defined above and at least one pharmaceutically acceptable excipient.

Another subject matter of the invention is a method for obtaining an intermediate product for obtaining the compounds defined above. The intermediate product is C20-aminosalinomycin with the following formula (3):

(3)

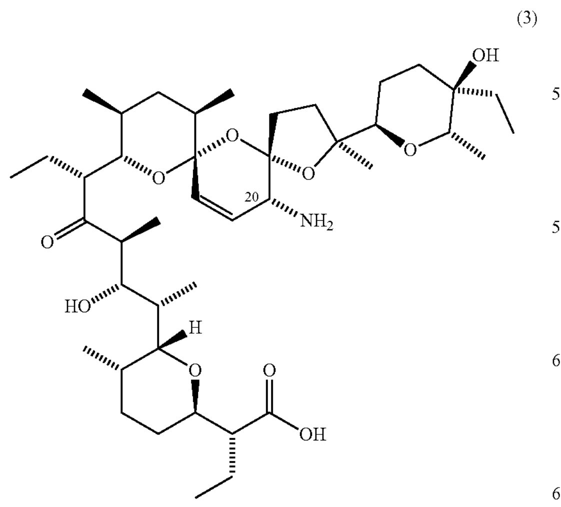

or a salt thereof. The method for obtaining this intermediate product involves the following steps:

a) chemoselective oxidation of the C20-hydroxy group of salinomycin with the formula (1):

(1)

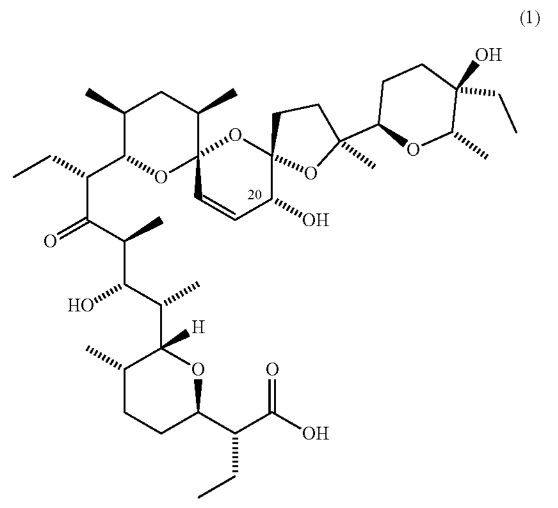 [SMILES: CC[C@@H](C(=O)[C@@H](C)[C@@H](O)[C@H](C)[C@@H]1O[C@@H]([C@@H](CC)C(=O)O)CC[C@@H]1C)[C@H]1O[C@]2(C=C[C@@H](O)[C@]3(CC[C@@](C)([C@H]4CC[C@](O)(CC)[C@H](C)O4)O3)O2)[C@H](C)C[C@@H]1C]

b) followed by stereoselective reductive amination of the resulting C20-oxosalinomycin with the formula (8):

(8)

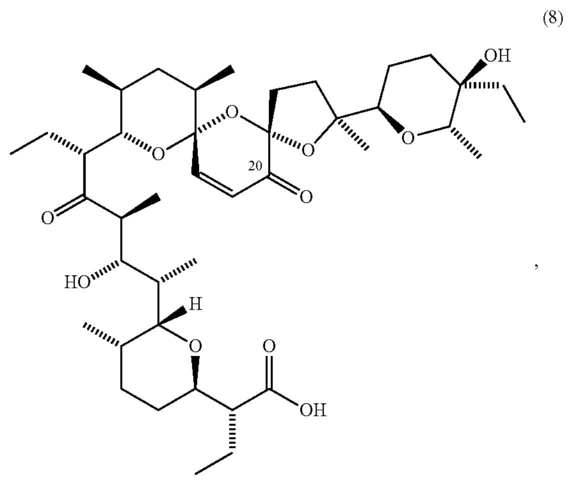

, wherein an alcoholic solution of ammonia is used as the aminating agent, resulting in the in situ formation of an imine derivative which is then reduced with sodium borohydride or a sodium borohydride derivative, in particular sodium cyanoborohydride, in the presence of a cerium salt.

Another subject matter of the invention is a method for obtaining the compounds defined above in the reaction between C20-aminosalinomycin with the formula (3):

(3)

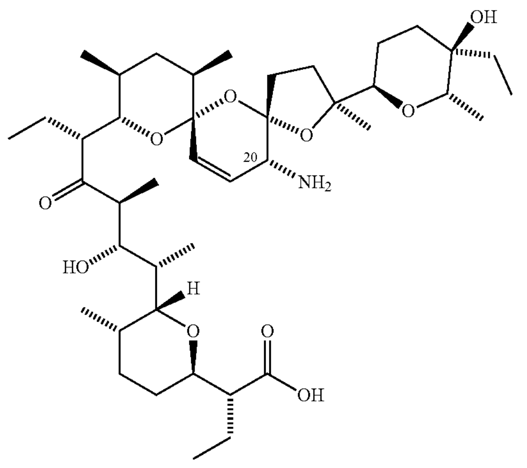

and:

acid chloride with the general formula (4):

(4)

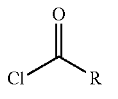

or carboxylic acid with the general formula (5):

(5)

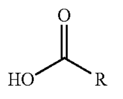

or chloroformate with the general formula (6):

(6)

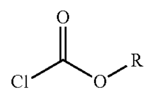

or isocyanate with the general formula (7):

(7)

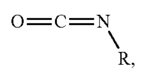

wherein R denotes:

a straight-chain or branched-chain alkyl group comprising 1 to 10 carbons, a straight-chain or branched-chain alkyl group comprising 1 to 10 carbons which is substituted at any position of the carbon chain by 1 to 5 halogens, which may be present at the same carbon or at different carbons, a straight-chain alkyl group comprising 2 to 10 carbons which comprises ether moiety at any position of the carbon chain, a straight-chain alkyl group comprising 3 to 10 carbons which comprises multiple bonds, either double or triple bonds, at any position of the carbon chain, a monocyclic, dicyclic or tricyclic alkyl group comprising 5 to 10 carbons, an aromatic aryl group, wherein those comprising a six-membered aromatic ring are preferred, an aromatic aryl group substituted by 1 to 3 substituents independently selected from alkyl, alkoxy, hydroxy, nitro and nitrile groups or halogens, an aromatic heteroaryl group, wherein 1 or more carbons are substituted by 1 or more heteroatoms from a group comprising atoms of oxygen, nitrogen or sulphur, an alkyl-aryl group, wherein the aromatic aryl group as defined above is linked to a salinomycin molecule by a carbon chain comprising 1 to 5 carbons (alkyl comprising 1-5 carbons);

optionally, comprising a step of transforming the resulting compound in acidic form into a salt thereof.

Preferably, the method for obtaining said compounds comprises the following:

a) in the first step, obtaining the intermediate product with the formula (3):

(3)

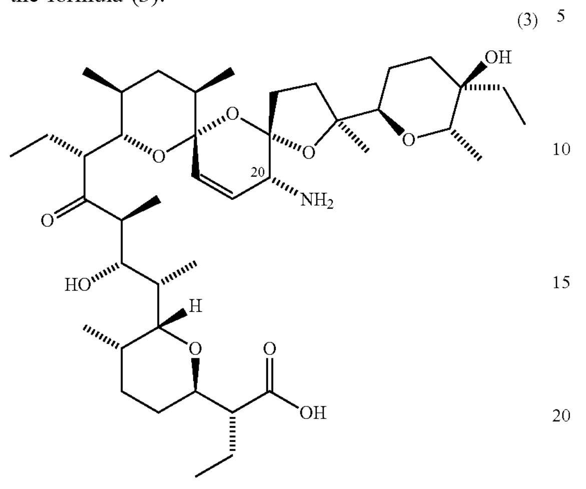

by the chemoselective oxidation reaction of the C20-hydroxy group of salinomycin with the formula (1):

(1)

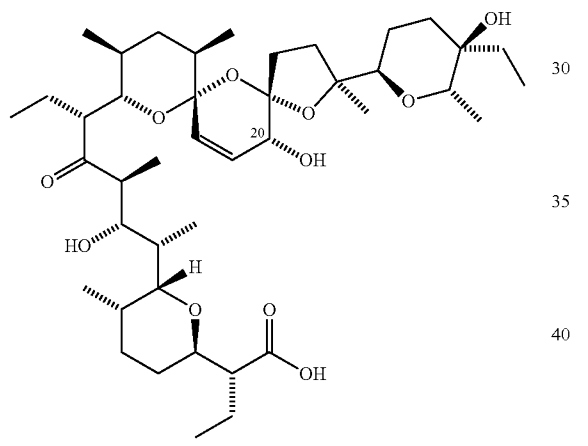

followed by stereoselective reductive amination of the resulting C20-oxosalinomycin with the formula (8):

(8)

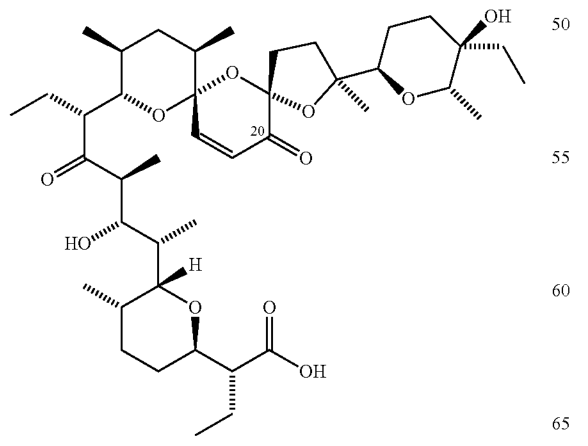

b) in the second step, obtaining a compound with the general formula (2):

(2)

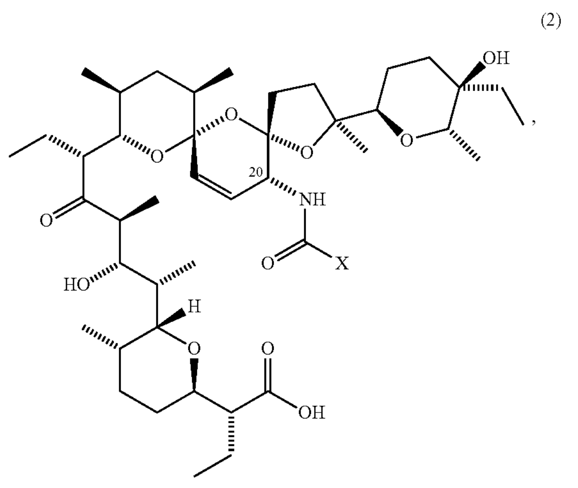

wherein:

X denotes R, O—R or NH—R;

R denotes:

a straight-chain or branched-chain alkyl group comprising 1 to 10 carbons, a straight-chain or branched-chain alkyl group comprising 1 to 10 carbons which is substituted at any position of the carbon chain by 1 to 5 halogens, which may be present at the same carbon or at different carbons, a straight-chain alkyl group comprising 2 to 10 carbons which comprises ether moiety at any position of the carbon chain, a straight-chain alkyl group comprising 3 to 10 carbons which comprises multiple bonds, either double or triple bonds, at any position of the carbon chain, a monocyclic, dicyclic or tricyclic alkyl group comprising 5 to 10 carbons, an aromatic aryl group, wherein those comprising a six-membered aromatic ring are preferred, an aromatic aryl group substituted by 1 to 3 substituents independently selected from alkyl, alkoxy, hydroxy, nitro and nitrile groups or halogens, an aromatic heteroaryl group, wherein 1 or more carbons are substituted by 1 or more heteroatoms from a group comprising atoms of oxygen, nitrogen or sulphur, or an alkyl-aryl group, wherein the aromatic aryl group as defined above is linked to a salinomycin molecule by a carbon chain comprising 1 to 5 carbons (alkyl comprising 1-5 carbons), by reacting C20-aminosalinomycin with the formula (3):

(3)

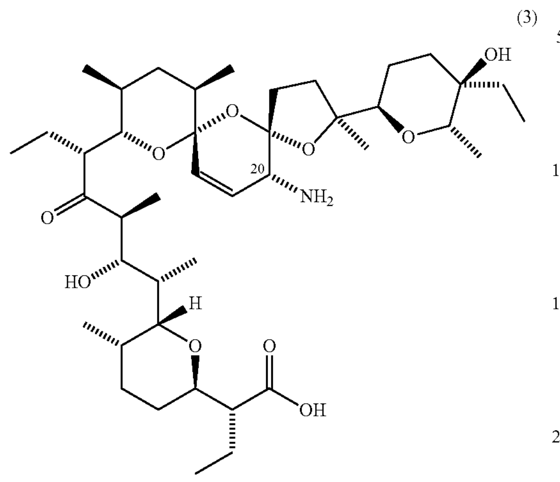

and:

acid chloride with the general formula (4):

(4)

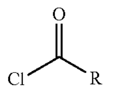

or carboxylic acid with the general formula (5):

(5)

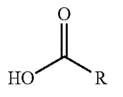

or chloroformate with the general formula (6):

(6)

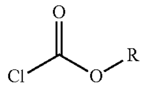

or isocyanate with the general formula (7):

(7)

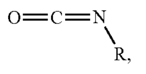

wherein R is as indicated above;

optionally, comprises a step of transforming the resulting compound in acidic form into a salt thereof.

The invention also relates to the compound defined above for use as a medicament. Preferably, the compound is for use as an anti-cancer agent. More preferably, the compound defined above is for use in treatment of conditions selected from the group comprising leukaemia, including without limitation acute myeloid leukaemia, chronic myeloid leukaemia, acute lymphoblastic leukaemia, multiple myeloma; non-small cell lung cancer, including without limitation lung epithelial cell carcinoma, lung adenocarcinoma, human lung squamous cell cancer; large intestine (colon) cancer, including without limitation large intestine adenocarcinoma, colon epithelial cell cancer; tumour of the central nervous system, including without limitation brain tumours such as glioma; melanoma, including without limitation malignant melanoma, epithelial melanoma, non-epithelial melanoma; ovarian cancer, including without limitation epithelial ovarian cancer, ovarian cystadenocarcinoma; kidney cancer, including without limitation renal cell carcinoma; prostate cancer, including without limitation prostate adenocarcinoma; breast cancer, including without limitation adenocarcinoma of the breast, inflammatory breast cancer, metastatic adenocarcinoma; stomach cancer; pancreatic cancer; sarcoma and uterine body cancer, as well as its drug-resistant variant; cervical cancer; bladder cancer.

More preferably, the compound is for use in treatment of conditions selected from the group of: melanoma, colon cancer, breast cancer and biphenotypic leukaemia.

DETAILED DESCRIPTION OF THE INVENTION

Preferred embodiments of the invention are disclosed in the following detailed description and in the accompanying claims. Various embodiments of the invention are defined herein in greater detail. Any of the aspects so defined may be combined with any other aspect or aspects, unless expressly stated otherwise. In particular, any of the features indicated as advantageous or preferable may be combined with any other feature or features indicated as advantageous or preferable.

Reference throughout the description to an “embodiment” or an “aspect” of the invention is to be understood that a particular feature, structure or characteristic described in connection with such an embodiment is comprised in at least one embodiment of the present invention. Thus, instances of the terms “embodiment” or “aspect” or “variant” in various places of this description may or may not refer to the same embodiment. Further, particular features, structures or characteristics may be combined in any suitable manner, as would be apparent to a person skilled in the art of this disclosure, in one or more embodiments. Moreover, although some aspects of the invention described herein include some features, not differing from those included in other embodiments, combinations of features from different embodiments are intended to be within the scope of the invention and they form different embodiments, as would be apparent to those skilled in the art. Any of the embodiments claimed may be used in any combination.

Most generally, the invention relates to compounds constituting C20-N-acyl (N-amide, N-carbamate (urethane) and urea) salinomycin derivatives with the general formula (2):

(2)

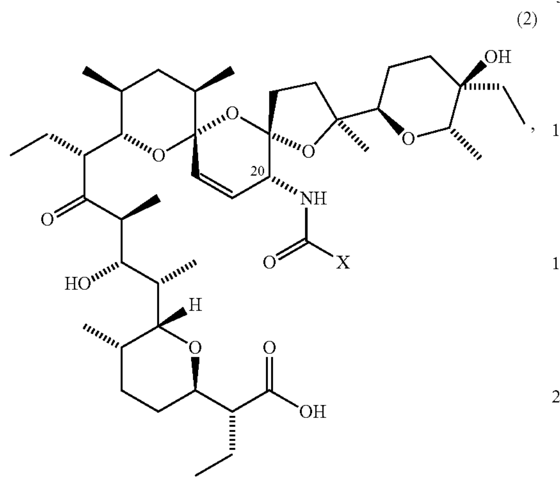

wherein:

X denotes R, O—R or NH—R, respectively;

R denotes:

- a straight-chain or branched-chain alkyl group comprising 1 to 10 carbons,
- a straight-chain or branched-chain alkyl group comprising 1 to 10 carbons which is substituted at any position of the carbon chain by 1 to 5 halogens, which may be present at the same carbon or at different carbons,
- a straight-chain alkyl group comprising 2 to 10 carbons which comprises ether moiety at any position of the carbon chain,
- a straight-chain alkyl group comprising 3 to 10 carbons which comprises multiple bonds, either double or triple bonds, at any position of the carbon chain,
- a monocyclic, dicyclic or tricyclic alkyl group comprising 5 to 10 carbons,
- an aromatic aryl group, wherein those comprising a six-membered aromatic ring are preferred,
- an aromatic aryl group substituted by 1 to 3 substituents independently selected from alkyl, alkoxy, hydroxy, nitro and nitrile groups or halogens,
- an aromatic heteroaryl group, wherein 1 or more carbons are substituted by 1 or more heteroatoms from a group comprising atoms of oxygen, nitrogen or sulphur,
- an alkyl-aryl group, wherein the aromatic aryl group as defined above is linked to a salinomycin molecule by a carbon chain comprising 1 to 5 carbons (alkyl comprising 1-5 carbons);

and salts thereof.

The compounds according to the invention have an absolute configuration R on the asymmetric C-20 carbon. The absolute configuration of the novel derivatives on the asymmetric C-20 carbon is the same as the absolute configuration on the asymmetric C-20 carbon of the starting salinomycin. Therefore, the preparation of the novel salinomycin derivatives according to the invention provides a retention of the configuration on the asymmetric C-20 carbon of salinomycin.

The X moiety in the compounds according to the invention may be R, O—R or NH—R.

Preferably, X denotes R. Then the salinomycin derivatives may be referred to as N-amide derivatives. Also preferably, R denotes O—R. The salinomycin derivatives may then be referred to as N-carbamate (urethane) derivatives. Also preferably, R may denote NH—R. The salinomycin derivatives may then be referred to as urea derivatives. For all types of the novel salinomycin derivatives recited herein, the R substituent is as defined in detail below, without limitations. It will be apparent to a person skilled in the art that other R substituents similar to those recited below, even to those recited as specific groups, are also within the scope of the invention.

In a preferred embodiment of the invention, the R substituent in the general formula (2) defining the compounds according to the invention is a straight-chain or branched-chain alkyl group comprising 1 to 10 carbons. Preferably, the R substituent is a straight-chain alkyl group. Also preferably, R is a branched-chain alkyl group. Preferably, the alkyl group comprises 1 to 10 carbons, more preferably 1 to 5 carbons, also more preferably 1 to 3 carbons.

Preferably, R is a methyl, ethyl, n-butyl, isopropyl, neopentyl residue.

In another preferred embodiment of the invention, the R substituent in the general formula (2) defining the compounds according to the invention is a straight-chain or branched-chain alkyl group comprising 1 to 10 carbons which is substituted at any position of the carbon chain by 1 to 5 halogens, which may be present at the same carbon or at different carbons. "Halogen" denotes an atom of fluorine (F), chlorine (Cl), bromine (Br) or iodine (I), in particular a chlorine. Preferably, the R substituent is a straight-chain alkyl group. Also preferably, R is a branched-chain alkyl group. Preferably, the alkyl group comprises 1 to 10 carbons, more preferably 1 to 5 carbons, also more preferably 1 to 3 carbons. Preferably, R is an alkyl monohalide. Also preferably, R is an alkyl dihalide or an alkyl trihalide. Preferably, R is a chloromethyl, 3-chloropropyl, 2,2,2-trichloroethyl moiety.

In another preferred embodiment, the R substituent in the general formula (2) defining the compounds according to the invention is a straight-chain alkyl group comprising 2 to 10 carbons which comprises ether moiety at any position of the carbon chain (ether moiety, —O—).

Preferably, the R substituent is a straight-chain alkyl group. Also preferably, R is a branched-chain alkyl group. Preferably, the alkyl group comprises 2 to 10 carbons, more preferably 2 to 5 carbons, also more preferably 2 to 3 carbons. The alkyl group may contain 1 to 3 ether moieties, preferably 2, and even more preferably one —O— group. Preferably, R is a dimethyl ether moiety.

In preferable variants of the invention, there may also be R groups constituting an alkyl group as defined above, comprising both one or more halogen substituent and an ether moiety. "Halogen" denotes an atom of fluorine (F), chlorine (Cl), bromine (Br) or iodine (I), in particular a chlorine. Preferably, R is an alkyl substituted with one halogen and comprising one ether moiety.

In another preferred embodiment, the R substituent in the general formula (2) defining the compounds according to the invention is a straight-chain alkyl group comprising 3 to 10 carbons which comprises multiple bonds, either double or triple bonds, at any position of the carbon chain. Preferably, the alkyl group comprises 3 to 10 carbons, more preferably 3 to 5 carbons, also more preferably 3 carbons. Preferably, the R group is a propargyl (prop-2-ynyl) moiety.

In another preferred embodiment of the invention, the R substituent in the general formula (2) defining the compounds according to the invention is a monocyclic, dicyclic or tricyclic alkyl group comprising 5 to 10 carbons. Preferably, the cyclic alkyl group may be substituted with a halogen. "Halogen" denotes an atom of fluorine (F), chlorine (Cl), bromine (Br) or iodine (I), in particular a chlorine. Preferably, R is adamantyl. R may also be a cyclopentyl or cyclohexyl substituent.

In another preferred embodiment of the invention, the R substituent in the general formula (2) defining the compounds according to the invention is an aromatic aryl group. Preferably, R is a six-membered aromatic ring. Preferably, R is a phenyl substituent.

In another preferred embodiment, the R substituent in the general formula (2) defining the compounds according to the invention is an aromatic aryl group substituted by 1 to 3 substituents independently selected from alkyl, alkoxy, hydroxy, nitro and nitrile groups or halogens. "Halogen" denotes an atom of fluorine (F), chlorine (Cl), bromine (Br) or iodine (I), in particular a chlorine. Preferably, the aryl group comprises two of the aforementioned substituents. These may be two halogens. They may also be two nitro groups. Also preferably, the aryl group comprises an alkyl substituted with one, two, or three halogens. Said groups may be in the ortho, meta or para position of the aryl group. Preferably, the R substituent is a para-chloromethylphenyl substituent.

In another preferred embodiment, the R substituent in the general formula (2) defining the compounds according to the invention is an aromatic heteroaryl group, wherein 1 or more carbons are substituted by 1 or more heteroatoms from a group comprising atoms of oxygen, nitrogen or sulphur. Preferably, the heteroatom is an atom of oxygen. Preferably, the heteroatom is an atom of sulphur. Preferably, the heteroatom is an atom of nitrogen. Preferably, the R substituent is a 1-furyl residue.

In another preferred embodiment, the R substituent in the general formula (2) defining the compounds according to the invention is an alkyl-aryl group, wherein the aromatic aryl group as defined above is linked to a salinomycin molecule by a carbon chain comprising 1 to 5 carbons. Preferably, the carbon chain is straight or branched.

Preferably, the compounds according to the invention may also be in the form of salts. The general formula of the salts of salinomycin derivatives according to the invention is illustrated by the general formula (2a):

(2a)

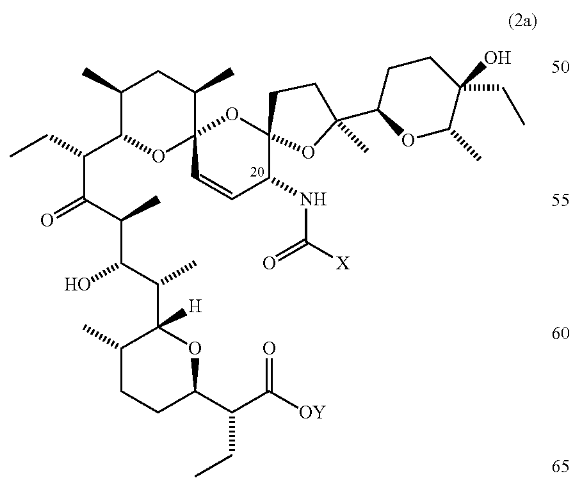

Preferred salts of the compounds according to the invention are sodium, potassium or lithium salt. Y in the general formula (2a) is then respectively: Na, K, Li. Preferably, Y denotes Na. The scope of the invention also includes salts with divalent metals, such as e.g. magnesium.

A person skilled in the art will know how to select and adjust the conditions for obtaining an acidic derivative or a desired salt thereof. Extraction of salinomycin and its derivatives with an aqueous solution of sulphuric(VI) acid or hydrochloric acid produces the acidic form (Y═H). Extraction of salinomycin and its derivatives with an aqueous solution of a suitable inorganic salt, in turn, yields compounds in the form of salts (Y═Na, K, Li). Preferably, to obtain the sodium, potassium or lithium salt of the compound according to the invention, extraction with sodium, potassium or lithium carbonate is used.

The invention also relates to a composition comprising the compound according to the invention and at least one pharmaceutically acceptable excipient. Pharmaceutically acceptable excipients are known in the art and are exemplified in Remington: The Science and Practice of Pharmacy 1995, ed. by E. W. Martin, Mack Publishing Company, 19 Edition, Easton, Pa.

Preferably, the composition comprises one compound according to the invention and at least one pharmaceutically acceptable excipient.

The invention also relates to a method for obtaining novel compounds according to the invention, C20-modified salinomycin derivatives, by reacting C20-aminosalinomycin (3) and compounds with the general formulas (4), (5), (6) or (7) according to the claims. For further clarification, this method will be explained for two preferred aspects:

- where the reactants are compounds with the general formula (4), (5) or (6),
- where the reactant is a compound with the general formula (7).

Thus, a preferred embodiment of the invention is a method for obtaining compounds according to the invention, such as: C20-N-amide and C20-N-carbamate (urethane) salinomycin derivatives with the general formula (2), where X denotes R or O—R, respectively, and R is as defined above, in the reaction between C20-aminosalinomycin with the formula (3):

(3)

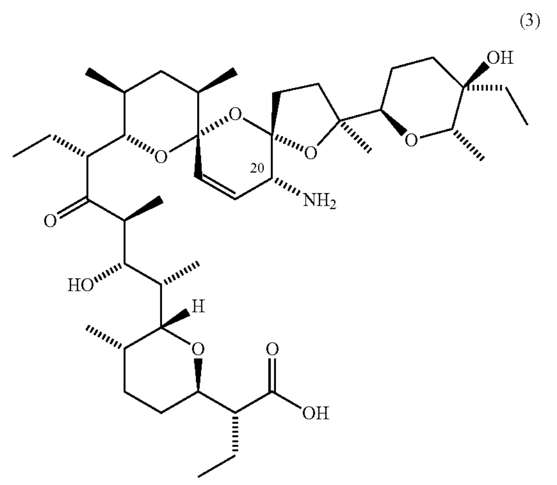

and acid chloride with the general formula (4):

(4)

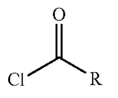

or carboxylic acid with the general formula (5):

(5)

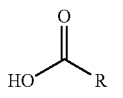

wherein R is as defined above.

(6)

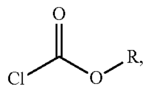

The method optionally comprises a step of transforming the resulting compound in acidic form into a salt thereof. A person skilled in the art will know how to select the reaction conditions for the conversion of a salinomycin derivative in acidic form into a salt thereof.

Correct order of adding the individual reactants is essential for successful reactions to obtain C20-N-amide and C20-N-carbamate (urethane) salinomycin derivatives with the general formula (2), where X denotes R or O—R, respectively, and R is as defined above. Due to the high susceptibility of salinomycin to acid chlorides with the general formula (4), chloroformates with the general formula (6) and the hydrogen chloride resulting from the reaction, both the acid chloride with the general formula (4), and the chloroformate with the general formula (6) are first mixed with 4-dimethylaminopyridine (DMAP) and a suitable aliphatic amine, and finally C20-aminosalinomycin with the formula (3) is added to the mixture according to the procedure described in detail below.

When using acid chlorides with the general formula (4) or chloroformates with the general formula (6), the reaction is carried out in apolar chloroaliphatic or aromatic solvent or in tetrahydrofuran, preferably in chloroform, methylene chloride, toluene, benzene, tetrahydrofuran, most preferably in chloroform or methylene chloride, or in an aprotic polar solvent such as simple nitrile, preferably in acetonitrile, or in a simple tertiary amide, preferably in N,N-dimethylformamide, in the presence of 4-dimethylaminopyridine (DMAP) acting as a reaction activator and an aliphatic amine. Also preferably, the reaction is conducted under anhydrous conditions. The aliphatic amine used is triethylamine, tripropylamine, tributylamine, diisopropylamine, triisopropylamine, triisobutylamine, N,N-diisopropylethylamine, most preferably triethylamine. Aliphatic amines complex the by-product resulting from the reaction, namely hydrogen chloride. The binding of hydrogen chloride by the aliphatic amine prevents undesired side reactions and prevents the irreversible decomposition of the compound with the formula (3).

In an initial step of the reaction, an aliphatic amine, preferably triethylamine, followed by acid chloride with the general formula (4) or chloroformate with the general formula (6) is added at 0° C. to a solution of 4-dimethylaminopyridine (DMAP) in an apolar chloroaliphatic or aromatic solvent, or in tetrahydrofuran, preferably in chloroform, methylene chloride, toluene, benzene, tetrahydrofuran, most preferably in chloroform or methylene chloride, or in a polar aprotic solvent such as simple nitrile, preferably in acetonitrile, or in a simple tertiary amide, preferably in N,N-dimethylformamide. This is mixed at reduced temperature (<5° C.) for 30 minutes, followed by adding C20-aminosalinomycin with the formula (3) previously dissolved in a minimum amount of apolar chloroaliphatic or aromatic solvent or in tetrahydrofuran, preferably in chloroform, methylene chloride, toluene, benzene, tetrahydrofuran, most preferably in chloroform or methylene chloride, or in a minimum amount of the aprotic polar solvent such as simple nitrile, preferably in acetonitrile, or in a simple tertiary amide, preferably in N,N-dimethylformamide. Given the risk of side reactions and the possibility of irreversible decomposition of the compound with the formula (3), the reaction should be carried out at a reduced temperature (<5° C.) for another 30 minutes. Cooling of the reaction system is then discontinued, the reaction mixture is let to warm up to room temperature and mixing is continued until the reaction is over, with the reaction completeness preferably being monitored by thin layer chromatography TLC.

The reaction mixture is then washed with an aqueous solution of sodium carbonate (0.1 M). The organic layer is evaporated under reduced pressure, and the residue is purified by column chromatography, preferably using a CombiFlash® chromatograph with an ELS detector, using a column filled with silica and a mixture of organic solvents, preferably a mixture of ethyl acetate:n-hexane with an increasing gradient of ethyl acetate concentration from 0% to 100%. The combined fractions containing the C20-N-amide or C20-N-carbamate (urethane) as the reaction product are evaporated until dry under reduced pressure, the residue is dissolved in an apolar chloroaliphatic solvent, preferably methylene chloride or chloroform, followed by extraction with an aqueous solution of a suitable salt (0.1 M), or with an aqueous solution of sulphuric(VI) acid or hydrochloric acid (pH=1.0) and finally with water. The combined organic layers are evaporated until dry under reduced pressure, and then repeatedly evaporated with n-pentane.

When carboxylic acids with the general formula (5) are used, it is essential for the success of the reaction that they are appropriately pre-activated with suitable coupling agents/activators according to the procedure described in detail below. The reaction is carried out in apolar chloroaliphatic or aromatic solvent or in tetrahydrofuran, preferably in chloroform, methylene chloride, toluene, benzene, tetrahydrofuran, most preferably in chloroform or methylene chloride, or in an aprotic polar solvent such as simple nitrile, preferably in acetonitrile, or in a simple tertiary amide, preferably in N,N-dimethylformamide. Also preferably, the reaction is conducted under anhydrous conditions and in the presence of a coupling agent. The coupling agent used is N,N'-dicyclohexylcarbodiimide (DCC), N,N'-diisopropylcarbodiimide (DIC), 1,1'-carbonyldiimidazole (CDI), 1-ethyl-3-(3'-dimethylaminopropyl)carbodiimide hydrochloride (EDC), 2-(7-aza-1H-benzotriazol-1-yl)-1,1,3,3-tetramethyluronium hexafluorophosphate (HATU), wherein, if N,N'-dicyclohexylcarbodiimide (DCC) is used, it is preferable to use also p-toluenesulfonic acid, N-hydroxysuccinimide, 3-hydroxy-4-keto-1,2,3-benzotriazine, N-hydroxybenzotriazole (HOBt), 4-dimethylaminopyridine (DMAP) or 4-pyrrolidinopyridine.

In the initial step of the reaction, a coupling agent is added to a solution of carboxylic acid with the general formula (5) in apolar chloroaliphatic or aromatic solvent or in tetrahydrofuran, preferably in chloroform, methylene chloride, toluene, benzene, tetrahydrofuran, most preferably in chloroform or methylene chloride, or in an aprotic polar solvent such as simple nitrile, preferably in acetonitrile, or in a simple tertiary amide, preferably in N,N-dimethylformamide, at room temperature. This is mixed at room temperature for 30 minutes, followed by adding C20-aminosalinomycin with the formula (3) previously dissolved in a minimum amount of apolar chloroaliphatic or aromatic solvent or in tetrahydrofuran, preferably in chloroform, methylene chloride, toluene, benzene, tetrahydrofuran, most preferably in chloroform or methylene chloride, or in a minimum amount of the aprotic polar solvent such as simple nitrile, preferably in acetonitrile, or in a simple tertiary amide, preferably in N,N-dimethylformamide. Mixing is continued at room temperature until the reaction is over, and the reaction completeness of the reactants is preferably monitored by thin layer TLC chromatography.

The reaction mixture is then evaporated under reduced pressure, and the residue is purified by column chromatography, preferably using a CombiFlash® chromatograph with an ELS detector, using a column filled with silica and a mixture of organic solvents, preferably a mixture of ethyl acetate:n-hexane with an increasing gradient of ethyl acetate concentration from 0% to 100%. The combined fractions containing the C20-N-amide reaction product are evaporated until dry under reduced pressure, the residue is dissolved in an apolar chloroaliphatic solvent, preferably methylene chloride or chloroform, followed by extraction with an aqueous solution of a suitable salt (0.1 M), or with an aqueous solution of sulphuric(VI) acid or hydrochloric acid (pH=1.0) and finally with water. The combined organic layers are evaporated until dry under reduced pressure, and then repeatedly evaporated with n-pentane.

In another mentioned preferred embodiment, the invention relates to a method for obtaining novel C20-urea salinomycin derivatives with the general formula (2), where X denotes NH—R, and R is as defined above, in a reaction between C20-aminosalinomycin with the formula (3):

(3)

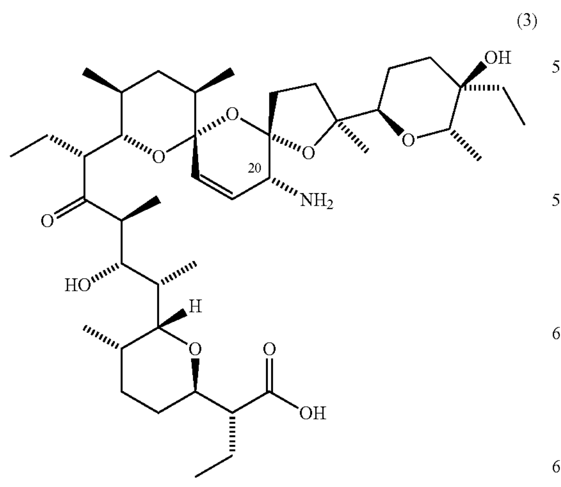

and isocyanate with the general formula (7):

(7)

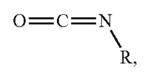

wherein R is as defined above.

The method optionally comprises a step of transforming the resulting compound in acidic form into a salt thereof. A person skilled in the art will know how to select the reaction conditions for the conversion of a salinomycin derivative in acidic form into a salt thereof.

The reaction with the isocyanate with the general formula (7) is carried out in apolar chloroaliphatic or aromatic solvent or in tetrahydrofuran, preferably in chloroform, methylene chloride, toluene, benzene, tetrahydrofuran, most preferably in chloroform or methylene chloride, or in an aprotic polar solvent such as simple nitrile, preferably in acetonitrile, or in a simple tertiary amide, preferably in N,N-dimethylformamide, at room temperature. Also preferably, the reaction is conducted under anhydrous conditions.

Once the reaction is over, reaction completeness is preferably monitored using thin layer chromatography TLC, the reaction mixture is washed with an aqueous solution of sodium bicarbonate (0.1 M). The organic layer is evaporated under reduced pressure, and the residue is purified by column chromatography, preferably using a CombiFlash® chromatograph with an ELS detector, using a column filled with silica and a mixture of organic solvents, preferably a mixture of ethyl acetate:n-hexane with an increasing gradient of ethyl acetate concentration from 0% to 100%. The combined fractions containing the C20-urea reaction product are evaporated until dry under reduced pressure, the residue is dissolved in an apolar chloroaliphatic solvent, preferably methylene chloride or chloroform, followed by extraction with an aqueous solution of a suitable salt (0.1 M), or with an aqueous solution of sulphuric(VI) acid or hydrochloric acid (pH=1.0) and finally with water. The combined organic layers are evaporated until dry under reduced pressure, and then repeatedly evaporated with n-pentane.

The invention also relates to a method for obtaining an intermediate product for the method for obtaining salinomycin derivatives modified at C-20 carbon. The three-step procedure for the synthesis of the intermediate compound with the formula (3) starts with the chemoselective oxidation of the C20-hydroxy group of salinomycin with the formula (1) taking place in an apolar chloroaliphatic solvent, preferably in methylene chloride or chloroform, at room temperature using activated manganese(TV) oxide [according to: EP3191493 or Mai et al., *Nature Chemistry,* 9, 2017, 1025-1033], followed by a two-step reductive amination of the resulting C20-oxosalinomycin [following the general procedure described in: EP3191493 or Mai et al., *Nature Chemistry,* 9, 2017, 1025-1033] with the formula (8):

(8)

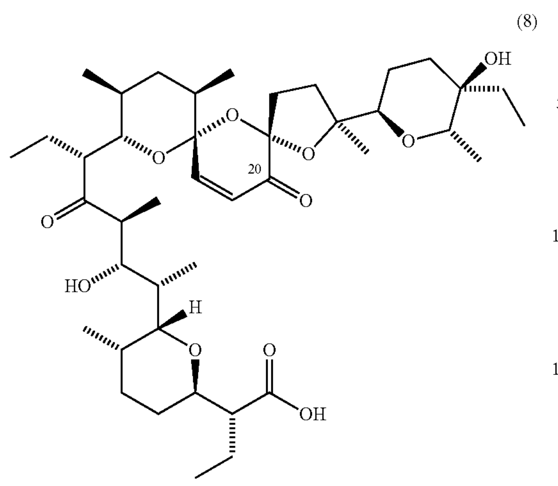

Conversion of the compound with the formula (8) into the compound with the formula (3) as broadly illustrated in prior art has been enhanced and modified for the purposes of the invention. The modified procedure for the preparation of the compound with the formula (8) comprises the use of an alcoholic solution of ammonia at a suitable concentration, as well as increasing the activation (imine formation) time to 5 hours. In the modified procedure, it is also no longer necessary to use acetic acid in the imine formation step or to treat the post-reaction mixture by liquid-liquid extraction, which significantly simplifies and accelerates the entire synthetic procedure.

In the first step of reductive amination, ammonia (7.0 N in methanol) reacts with C20-oxosalinomycin with the formula (8) dissolved in an alcoholic solvent, preferably methanol or ethanol, at room temperature to form imine in situ. According to the Luche reduction, in the second reductive amination step, the reaction intermediate product (imine) is reduced by slowly adding sodium borohydride or a sodium borohydride derivative, in particular sodium cyanoborohydride, in the presence of cerium salts, preferably cerium(III) chloride, to obtain C20-aminosalinomycin with the formula (3).

The invention also relates to the use of the novel salinomycin derivatives according to the invention for use as a medicament. In a preferred embodiment, the compounds according to the invention are intended for use as anti-cancer agents.

The compound according to the invention is suitable for use in conditions selected without limitations from the group comprising leukaemia, including without limitation acute myeloid leukaemia, chronic myeloid leukaemia, acute lymphoblastic leukaemia, biphenotypic leukaemia, multiple myeloma; non-small cell lung cancer, including without limitation lung epithelial cell carcinoma, lung adenocarcinoma, human lung squamous cell cancer; large intestine (colon) cancer, including without limitation large intestine adenocarcinoma, colon epithelial cell cancer; tumour of the central nervous system, including without limitation brain tumours such as glioma; melanoma, including without limitation malignant melanoma, epithelial melanoma, non-epithelial melanoma; ovarian cancer, including without limitation epithelial ovarian cancer, ovarian cystadenocarcinoma; kidney cancer, including without limitation renal cell carcinoma; prostate cancer, including without limitation prostate adenocarcinoma; breast cancer, including without limitation adenocarcinoma of the breast, inflammatory breast cancer, metastatic adenocarcinoma; stomach cancer; pancreatic cancer; sarcoma and uterine body cancer, as well as its drug-resistant variant; cervical cancer; bladder cancer.

In this description, the terms "cancer", ""tumor", "neoplasm" and "carcinoma" are used interchangeably.

Preliminary studies indicate that the compounds according to the invention have anti-cancer activity against the cell lines recited below:

HL-60(TB), K-562, MOLT-4, RPMI-8226, SR, A549/ATCC, EKVX, HOP-62, HOP-92, NCI-H226, NCI-H23, NCI-H460, NCI-H522, COLO 205, HCC-2998, HCT-116, HCT-15, HT29. KM12, SW-620, SF-268, SF-295, SF-539, SNB-19, SNB-75, U251, LOX IMVI, MALME-3M, M14, MDA-MB-435, SK-MEL-2, SK-MEL-28, SK-MEL-5, UACC-257, UACC-62, IGROVI, OVCAR-3, OVCAR-4, OVCAR-5, OVCAR-8, NCI/ADR-RES, SK-OV-3, 786-0, A498, ACHN, CAKI-1, RXF 393, SN12C, TK-10, UO-31, PC-3, DU-145, MCF7, MDA-MB-231/ATCC, HS 578T, BT-549, T-47D, MDA-MB-468, KATOIII, NCI-N87, SNU-16, SNU-5, AGS, SNU-1, Capan-2, ATCC HTB-80, Panc 10.05, CFPAC-1, HPAF-II, SW 1990, BxPC-3, AsPC-1, MES-SA, MES-SA/DX5, KLE, HEC-1-A, AN3 CA, Ca-Ski, DoTc2 4510, SiHa, C-33-A, 5637, KU-19-19, MBT-2, HCV29T, Hu1703He. For some of these cell lines, the specific associated conditions have already been recited in the list above.

Anti-cancer activity is understood as:

preventing cancer development, inhibiting cancer cell growth (inhibiting proliferation), inducing cancer cell death (pro-apoptotic effect), preventing or inhibiting cancer cell metastasis, inhibiting the phenomenon of multi-drug resistance, inhibiting the angiogenesis process, eliminating or minimising the impact of neoplastic disease.

In vitro studies conducted on a number of cancer cell lines confirmed high cytotoxic activity of the newly prepared compounds, which greatly exceeded the bioactivity of a chemically unmodified salinomycin. The salinomycin derivatives obtained not only demonstrate high anti-cancer activity, but also high selectivity of action against cancer cells.

Moreover, comparison of the anti-cancer activity and toxicity of the newly synthesized compounds with those exhibited by the salinomycin derivatives known from prior art, including the structurally similar C20-N-amide and C20-N-carbamate (urethane) derivatives of C20-epi-salinomycin with an inverted absolute configuration (S instead of R absolute configuration) on the asymmetric carbon at the C-20 position [Li et al., *European Journal of Medicinal Chemistry,* 148, 2018, 279-290], clearly demonstrated the superiority of the compounds that are the subject matter of the present invention in the context of their potential therapeutic use.

The following cancer cell lines were used in in vitro studies:

B16-F0 (murine melanoma),

Hs294T (human melanoma),

LoVo (drug-sensitive human colon cancer),

LoVo/DX (drug-resistant human colon cancer),

MCF-7 (human breast cancer),

MV-4-11 (human biphenotypic leukaemia).

Normal murine BALB/3T3 fibroblasts were also used in the tests for determining the selectivity coefficients of the compounds used in the assays. These values allow for predicting the direction of action of salinomycin derivatives by answering the question whether these compounds will first destroy cancer cells or attack normal body cells.

Table 1 summarises the data for all cell lines (both cancer and normal) used in the in vitro studies.

TABLE 1

| Cell line symbol | Cell line name | Source of origin of the cell line | Number of cells per well in the test |
|---|---|---|---|
| B16-F0 | murine melanoma | ATCC | $0.25 \times 10^4$ |
| Hs294T | human melanoma | ATCC | $0.20 \times 10^4$ |
| LoVo | drug-sensitive human colon cancer | ATCC | $1.00 \times 10^4$ |
| LoVo/DX | drug-resistant human colon cancer | Prof. E. Borowski, Politechnika Gdańska (Gdańsk University of Technology) | $1.00 \times 10^4$ |
| MCF-7 | human breast cancer | ECACC | $0.75 \times 10^4$ |
| MV-4-11 | human biphenotypic leukaemia | ATCC | $1.00 \times 10^4$ |
| BALB/3T3 | normal murine fibroblasts | ATCC | $1.00 \times 10^4$ |

During the in vitro cytotoxicity tests, the culture media and reagents summarised in Table 2 were used.

TABLE 2

| Name | Manufacturer |
|---|---|
| culture medium for B16-F0 line | OptiMEM (PChO, IITD PAN, Poland),<br>RPMI 1640 + HEPES (PChO, IITD PAN, Poland),<br>5% FBS (Sigma-Aldrich, Germany),<br>2 mM L-glutamine (Sigma-Aldrich, Germany),<br>0.5 mM sodium pyruvate (Sigma-Aldrich, Germany),<br>4.5 g/L glucose (Sigma-Aldrich, Germany),<br>0.1 mg/mL streptomycin, 100 U/mL penicillin (Sigma-Aldrich, Germany and Polfa Tarchomin, Poland) |
| culture medium for Hs294T line | RPMI 1640 W/GLUTAMAX-1 (Gibco, UK),<br>OptiMEM W/GLUTAMAX (Invitrogen, USA),<br>10% FBS (Sigma-Aldrich, Germany),<br>5.5 g/L glucose (Sigma-Aldrich, Germany),<br>0.1 mg/mL streptomycin, 100 U/mL penicillin (Sigma-Aldrich, Germany and Polfa Tarchomin, Poland) |
| culture medium for LoVo line | OptiMEM + RPMI1640 (1:1) (PChO, IITD PAN, Poland),<br>5% FBS HyClone (GE Healthcare, USA),<br>2 mM L-glutamine (Sigma-Aldrich, Germany),<br>1 mM sodium pyruvate (Sigma-Aldrich, Germany),<br>0.1 mg/mL streptomycin, 100 U/mL penicillin (Sigma-Aldrich, Germany and Polfa Tarchomin, Poland) |
| culture medium for LoVo/DX line | medium for LoVo/DX line as for LoVo line; additionally doxorubicin (Accord, UK) at 10 μg/100 mL medium |
| culture medium for MCF-7 line | Eagle medium (PChO, IITD PAN, Poland),<br>10% FBS (Sigma-Aldrich, Germany),<br>2 mM L-glutamine (Sigma-Aldrich, Germany),<br>1% amino acids (Sigma-Aldrich, Germany),<br>8 μg/mL insulin (Sigma-Aldrich, Germany),<br>0.1 mg/mL streptomycin, 100 U/mL penicillin (Sigma-Aldrich, Germany and Polfa Tarchomin, Poland) |
| culture medium for MV-4-11 line | RPMI 1640 W/GLUTAMAX-I (Gibco, UK),<br>10% FBS (Sigma-Aldrich, Germany),<br>1 mM sodium pyruvate (Sigma-Aldrich, Germany),<br>0.1 mg/mL streptomycin, 100 U/mL penicillin (Sigma-Aldrich, Germany and Polfa Tarchomin, Poland) |
| culture medium for BALB/3T3 line | Dulbecco medium (Gibco, UK),<br>10% FBS HyClone (GE Healthcare, USA),<br>2 mM L-glutamine (Sigma-Aldrich, Germany),<br>0.1 mg/mL streptomycin, 100 U/mL penicillin (Sigma-Aldrich, Germany and Polfa Tarchomin, Poland) |
| test medium for dilutions | RPMI1640 + HEPES (PChO, IITD PAN, Poland),<br>10% FBS HyClone (GE Healthcare, USA),<br>2 mM L-glutamine (Sigma-Aldrich, Germany),<br>0.1 mg/mL streptomycin, 100 U/mL penicillin (Sigma-Aldrich, Germany and Polfa Tarchomin, Poland) |
| 10 mM TRIS | deionised water, for general laboratory purposes, non-sterile, TRIZMA BASE (Sigma-Aldrich, Germany) |
| 1% acetic acid | deionised water, for general laboratory purposes, non-sterile, acetic acid 80%, analytical grade (POCH S.A., Poland) |
| 50% trichloroacetic acid | deionised water, for general laboratory purposes, non-sterile, trichloroacetic acid, analytical grade (POCH S.A., Poland) (a solid to be weighed and dissolved in water to achieve a 50% concentration) |
| 0.1% sulforhodamine B (SRB) solution | sulforhodamine B sodium salt (Sigma-Aldrich, Germany),<br>1% acetic acid |
| MTT | thiazolyl blue - tetrazolium bromide, ~98% (Sigma-Aldrich, Germany),<br>PBS (PChO, IITD PAN, Poland) |

TABLE 2-continued

| Name | Manufacturer |
|---|---|
| lysis buffer for MTT | MilliQ UF Plus water, sodium dodecyl sulphate (Sigma-Aldrich, Germany), N,N-dimethylformamide, analytical grade (POCH S.A., Poland) |
| cisplatin | concentrate for solution for infusion, 1 mg/mL (10 mg/10 mL), 1 of 10 mL vial (Teva Pharmaceuticals, Poland) |

In vitro cytotoxicity tests were performed according to the procedure described below. Stock solutions of the test compounds at 10 mg/mLh were prepared for each experiment ex tempore by dissolving 1 mg of the preparation in 100 μL of dimethylsulfoxide (DMSO). The solvent for further dilutions was a culture medium. Compounds were tested at concentration ranges of 100 to 0.00001 μg/mLh (for the B16-F0 and Hs294T cell lines) and 100 to 0.1 μg/mLh (for the LoVo, LoVo/DX, MCF-7, MV-4-11 and BALB/3T3 cell lines).

The assays of the cytotoxic effects of the tested compounds and the reference compound—cisplatin (a commonly used anti-cancer drug) were carried out in 96-hour in vitro cultures. An MTT tetrazolium salt reduction assay [as per: Wietrzyk et al., *Anti-cancer drugs,* 2007, 18, 447-457] was performed for MV-4-11 cells (human biphenotypic leukaemia) to evaluate the metabolic activity of cancer cells. On the other hand, to determine the anti-proliferative activity of all tested compounds against B16-F0 (murine melanoma), Hs294T (human melanoma), LoVo (drug-sensitive human colon cancer), LoVo/DX (drug-resistant human colon cancer), MCF-7 (human breast cancer) and BALB/3T3 (normal mouse fibroblasts) cell lines, the SRB colorimetric assay was used [as per: Skehan et al., *Journal of the National Cancer Institute,* 1990, 82, 1107-1112] measuring the inhibition of target cell proliferation based on the amount of cellular protein measured. In each experiment, samples containing specific concentrations of the test compound were applied to 96-well plates in triplicate. The experiments were repeated at least 3 times. In vitro cytotoxicity tests were performed according to the following procedure:

(a) Cells (derived from in vitro culture) were plated into the wells of a plate at $0.20\times10^4$ density (line Hs294T), $0.25\times10^4$ (line B16-F0), $0.75\times10^4$ (line MCF-7) or $1.00\times10^4$ (line LoVo, LoVo/DX, MV-4-11 and BALB/3T3) cells in 100 μL of culture medium and then incubated at 37° C. in a humid atmosphere (85-95% humidity) saturated with 5% carbon dioxide ($CO_2$), (b) after 24 hours, another 100 μL of the medium (cell growth control) or the medium containing the test compounds at the specified concentrations was added to the wells, (c) the plates were incubated for another 72 hours in an incubator (37° C., humid atmosphere (85-95% humidity) saturated with 5% $CO_2$), (d) after 72 hours of incubation of the cells with the test compounds, the MTT or SRB assay was performed, (e) in each experiment, samples containing determined concentrations of the test compound were applied in triplicate, and the experiments were reproduced 3 to 5 times.

MTT reading: 20 μL of MTT solution was added to each well of the 96-well plate. After 4 hours of incubation at 37° C., 80 μL of lysis buffer was added to each well. After another 24 hours of incubation at 37° C., optical density of individual samples was read at 570 nm using a Synergy H4 (universal) plate reader (BioTek Instruments, USA).

SRB reading: 50 μL of cold 50% trichloroacetic acid was added to each well of the 96-well plate. After 60 minutes of incubation at room temperature, the plates were washed 4 times with water and then dried on paper towels. 50 μL of a 0.1% solution of sulforhodamine B (SRB) in 1% acetic acid was then added to each well to stain the cell protein precipitated in the well. After a 30 min. incubation with SRB at room temperature, the plates were washed 4 times with 1% acetic acid and dried again on paper towels. In the next step, 150 μL of 10 mM TRIS buffer was added to each well to dissolve the dye bound with the cell protein. The optical density of individual samples was read at 540 nm using a Synergy H4 (universal) plate reader (BioTek Instruments, USA).

The inhibition of proliferation was calculated as a percentage for each test compound at a given concentration based on the measurement of the absorbance of individual wells using the following equation:

$$\text{percentage of proliferation inhibition} = \left(\left(\frac{A_t - A_m}{A_k - A_m}\right) \times 100\right) - 100,$$

wherein:

$A_m$—mean absorbance value of the control medium, $A_k$—mean absorbance value of control cells, i.e. untreated cells, $A_t$—mean absorbance value of cells treated with test compounds at a particular concentration.

When calculating the mean absorbance value for a set of wells (untreated cells, cells treated with a specific compound at a specific concentration, control of medium alone), outliers were rejected using a 10% coefficient of variation CV. The percentage inhibition of proliferation data was used to determine $IC_{50}$ values, i.e. the concentration of the test compound required to inhibit cell growth by 50% [as per: Nevozhay, *PLoS One,* 2014, 9, e106186]. Mean $IC_{50}$ values were then calculated based on another 3 to 5 replicates of the test, together with standard deviation values.

For comparative purposes, analogous studies were conducted using a commonly used anti-cancer drug, i.e. cisplatin. The results of the in vitro cytotoxic activity of the test compounds are presented as $IC_{50}$ values expressed in micromole concentrations (μM), which have been summarised in Table 3. All the newly obtained salinomycin derivatives have a very high anti-cancer activity, which in most cases significantly exceeds that of the chemically unmodified salinomycin with the formula (1), C20-aminosalinomycin with the formula (3), as well as the reference oncology drug cisplatin. Moreover, unlike salinomycin, most of the newly synthesised derivatives of this ionophore have been identified as anti-cancer agents capable of effectively overcoming the drug resistance of the cancer cells under consideration with RI drug resistance index values of <1.0. All newly obtained salinomycin derivatives are characterised by high selectivity of action towards cancer cells, which is manifested by selectivity coefficients SI>3.0, while some of them have been identified as extremely highly selective compounds (SI>100.0). This clearly indicates that the effect of the newly synthesised salinomycin derivatives against cancer cells is by far superior to that of their toxicity against normal body cells. B16-F0 (murine melanoma), Hs294T (human melanoma), LoVo (drug-sensitive human colon cancer), LoVo/DX (drug-resistant human colon cancer), MCF-7 (human breast cancer), MV-4-11 (human biphenotypic leukaemia), BALB/3T3 (normal murine fibroblasts);

$IC_{50}$ value—concentration of a compound corresponding to 50% inhibition of growth of cells used in the tests; SI>1.0 compound has a stronger cytotoxic effect against cancer cells than against normal cells; RI<2, cells sensitive to the tested compound, RI of 2-10 cells have moderate sensitivity to the test compound, RI>10 denotes a strong resistance to the test compound;

the value of the selectivity coefficient SI was calculated using the following equation:

$$SI = \frac{IC_{50} \text{ for normal cell line } BALB/3T3}{IC_{50} \text{ for particular cancer cell lines}}$$

the value of drug resistance coefficient RI was calculated using the following equation:

$$RI = \frac{IC_{50} \text{ for drug-resistant cancer cell line } LoVo/DX}{IC_{50} \text{ for drug-sensitive cancer cell line } LoVo}$$

Table 3 clearly shows that the compounds according to the invention have an anti-cancer activity against cancer cells from various tissues and organs. Moreover, the derivatives obtained have an anti-proliferative effect that is several times more potent compared to the parent compound, e.g. derivatives with the formulae (10), (15), (17), or an anti-proliferative effect that is even tens of times more potent, e.g. compounds with the formulae (21), (22), (25). The results of activity tests carried out on drug-sensitive and drug-resistant human colon cancer cells indicate that the compounds according to the invention can overcome drug resistance of cancer cells. Furthermore, the compounds according to the invention are characterised by an excellent selectivity of action, which demonstrates their extensive therapeutic potential. A person skilled in the art will know how to select a particular derivative to treat the appropriate type of cancer. As an example, it should be indicated that e.g. the derivative with the formula (21) has preferred effect against melanoma cells, while the compound with the formula (25) has preferred effect against biphenotypic leukaemia cells.

The compounds according to the invention and the methods for preparing the same are illustrated in the following examples. Said examples, rather than being intended to limit the scope of protection, only present selected, representative examples of embodiments of the invention. It will be within the knowledge of a person skilled in the art to select reactants and adjust reaction conditions to obtain other derivatives within the scope of protection as defined in the patent claims.

Example 1

Preparation of C20-dehydroxy-C20-aminosalinomycin N-acetamide with the Formula (9)

(9)

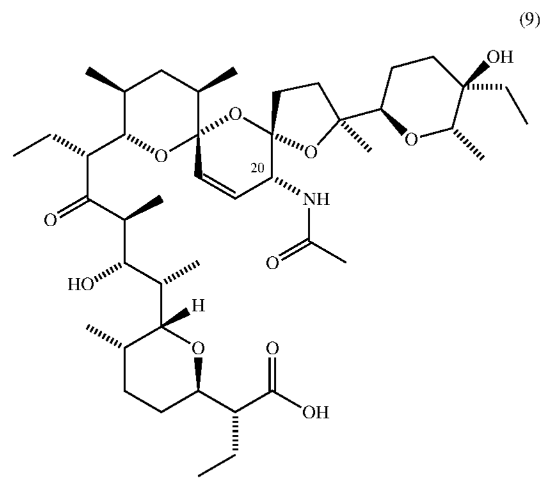

Triethylamine (8 mg, 1.2 eq.) and acetyl chloride (7 mg, 1.2 eq.) were added to a solution of 4-dimethylaminopyridine (10 mg, 1.2 eq.) in anhydrous methylene chloride (7 mL) cooled to a temperature of 0° C. and this was stirred for 30 minutes at reduced temperature (<5° C.). C20-aminosalinomycin (50 mg, 1.0 eq.), previously dissolved in a minimum amount of anhydrous methylene chloride was then added to the reaction mixture and stirred at reduced temperature (<5° C.) for another 30 minutes. This was then allowed to warm up to room temperature, and mixing was continued until the reaction was over, which was monitored by thin-layer chromatography TLC.

Once the reaction was over, the reaction mixture was washed with an aqueous solution of sodium carbonate (0.1 M). The organic layer was evaporated until dry under reduced pressure and the residue was purified using a CombiFlash® chromatograph with ELS detector, using a silica-filled column and a solvent mixture of ethyl acetate: n-hexane with an increasing gradient of ethyl acetate concentration from 0% to 100%. The combined fractions containing C20-dehydroxy-C20-aminosalinomycin N-acetamide with the formula (9) were evaporated until dry under reduced pressure, the residue was dissolved in methylene chloride and then extracted with an aqueous solution of sulphuric(VI) acid (pH=1.0) and finally with water. The combined organic layers were evaporated again until dry under reduced pressure, and then repeatedly evaporated with n-pentane. C20-dehydroxy-C20-aminosalinomycin N-acetamide with the formula (9) was obtained as a white amorphous solid with 72% yield.

Yield: 38 mg, 72%. Isolated as a white, amorphous solid; purity >95% by NMR and a single spot on TLC.

Rf: 0.54 in ethyl acetate 100%. Green spots in phosphomolybdic acid (PMA).

$^{13}C$ NMR (101 MHz, $CDCl_3$) δ 215.4, 177.7, 170.2, 129.3, 122.9, 105.4, 99.4, 88.4, 77.3, 77.2, 75.5, 74.9, 73.8, 71.7, 71.0, 68.4, 56.1, 49.7, 48.9, 48.6, 41.0, 38.5, 36.8, 36.3, 32.6, 30.5, 29.0, 28.0, 26.2, 26.0, 23.1, 22.6, 22.0, 20.0, 17.9, 16.4, 15.8, 14.7, 13.2, 12.9, 12.0, 11.2, 6.9, 6.3 ppm.

$^{1}H$ NMR (403 MHz, $CDCl_3$) δ ~13.00 (s, very br, 1H), 6.93 (d. J=8.0 Hz. 1H), 6.03 (dd. J=10.7, 2.6 Hz. 1H), 5.78 (dd. J=10.6, 2.0 Hz, 1H), 4.41 (dt, J=8.0, 2.3 Hz, 1H), 4.08 (dd. J=10.1, 1.4 Hz, 1H), 3.92 (dd. J=10.8, 5.4 Hz, 1H), 3.84 (dd. J=8.9, 5.3 Hz, 1H), 3.80 (d, J=10.3 Hz, 1H), 3.75 (dd. J=14.0, 7.0 Hz, 1H), 3.57 (dd. J=9.9, 1.8 Hz, 1H), 2.83 (td. J=10.8, 3.8 Hz, 1H), 2.67 (dq. J=9.8, 7.1 Hz, 1H), 2.52 (dd. J=11.1, 2.1 Hz, 1H), 2.10-0.50 (m, 56H), 1.91 (s. J=7.4 Hz, 3H) ppm.

ESI-MS (m/z): $[M+Na]^+$ calculated for $C_{44}H_{73}NNaO_{11}{}^+$ 814.5; found 814.

Example 2

Preparation of C20-dehydroxy-C20-aminosalinomycin N-isobutyramide with the Formula (10)

(10)

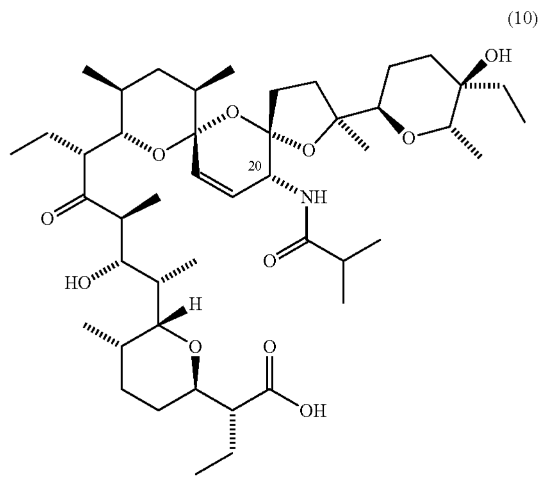

Proceeding as in example 1, except that instead of acetyl chloride (1.2 eq), isobutyryl chloride (9 mg, 1.2 eq) was added to the reaction mixture. C20-dehydroxy-C20-aminosalinomycin N-isobutyramide with the formula (10) was obtained as a white amorphous solid with 29% yield.

Yield: 16 mg, 29%. Isolated as a white, amorphous solid; purity >95% by NMR and a single spot on TLC.

Rf: 0.55 in ethyl acetate/n-hexane 50%. Green spots in phosphomolybdic acid (PMA).

$^{13}C$ NMR (101 MHz, $CD_2Cl_2$) δ 215.8, 177.7, 177.4, 130.2, 123.3, 106.0, 100.0, 89.0, 77.8, 76.1, 75.2, 73.8, 72.1, 71.2, 69.0, 56.3, 49.9, 49.2, 48.8, 41.5, 39.0, 37.2, 36.6, 35.7, 33.2, 30.9, 30.9, 29.2, 28.5, 26.6, 26.1, 23.1, 22.5, 20.4, 20.0, 19.6, 18.0, 16.7, 15.9, 15.0, 13.4, 13.2, 12.1, 11.3, 7.1, 6.5 ppm.

$^{1}H$ NMR (403 MHz, $CD_2Cl_2$) δ ~13.00 (s, very br, 1H), 6.78 (d, J=7.9 Hz, 1H), 6.07 (dd, J=10.7, 2.6 Hz, 1H), 5.76 (dd, J=10.6, 2.1 Hz, 1H), 4.39 (dt, J=7.9, 2.3 Hz, 1H), 4.07 (dd, J=10.1, 1.4 Hz, 1H), 3.95-3.81 (m, 3H), 3.76 (dd, J=13.9, 6.9 Hz, 1H), 3.58 (dd, J=10.0, 2.0 Hz, 1H), 2.89 (td, J=10.7, 4.0 Hz, 1H), 2.73 (dq, J=10.0, 7.1 Hz, 1H), 2.61 (dd, J=10.9, 1.9 Hz, 1H), 2.30 (dt, J=13.6, 6.8 Hz, 1H), 2.21-0.55 (m, 62H) ppm.

ESI-MS (m/z): $[M+Na]^+$ calculated for $C_{46}H_{77}NNaO_{11}{}^+$ 842.5; found 842.

Example 3

Preparation of C20-dehydroxy-C20-aminosalinomycin N-chloroacetamide with the Formula (11)

(11)

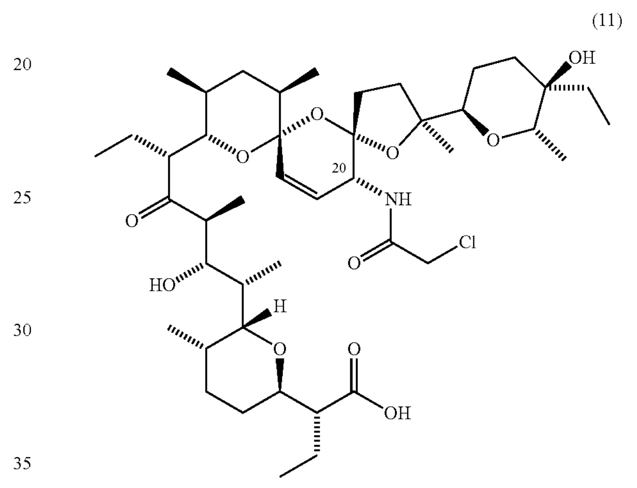

Proceeding as in example 1, except that instead of acetyl chloride (1.2 eq), chloroacetyl chloride (9 mg, 1.2 eq) was added to the reaction mixture. C20-dehydroxy-C20-aminosalinomycin N-chloroacetamide with the formula (11) was obtained as a white amorphous solid with 30% yield.

Yield: 17 mg, 30%. Isolated as a white, amorphous solid; purity >95% by NMR and a single spot on TLC.

Rf: 0.71 in ethyl acetate/n-hexane 50%. Green spots in phosphomolybdic acid (PMA).

$^{13}C$ NMR (101 MHz, $CD_2Cl_2$) δ 215.6, 177.8, 167.0, 129.0, 124.6, 105.9, 99.9, 88.9, 77.7, 76.4, 75.1, 73.5, 72.2, 71.3, 69.0, 56.1, 49.71, 49.69, 48.8, 43.2, 41.2, 38.9, 37.3, 36.5, 33.1, 31.4, 30.9, 29.3, 28.6, 26.6, 25.4, 23.0, 22.2, 20.4, 17.9, 16.7, 15.8, 14.9, 13.3, 13.2, 12.1, 11.4, 7.2, 6.5 ppm.

$^{1}H$ NMR (403 MHz, $CD_2Cl_2$) δ ~13.00 (s, very br, 1H), 7.23 (d, J=8.5 Hz, 1H), 6.14 (dd, J=10.6, 2.5 Hz, 1H), 5.79 (dd, J=10.6, 2.4 Hz, 1H), 4.50 (dt, J=8.6, 2.4 Hz, 1H), 4.07 (dd, J=10.1, 1.3 Hz, 1H), 4.00 (s, J=13.8 Hz, 2H), 3.92 (dd, J=10.8, 5.3 Hz, 1H), 3.79 (ddd, J=14.0, 8.4, 3.0 Hz, 3H), 3.58 (dd, J=9.9, 1.9 Hz, 1H), 2.89 (td, J=10.7, 4.1 Hz, 1H), 2.73 (ddd, J=14.3, 10.0, 7.1 Hz, 1H), 2.60 (dd, J=10.8, 1.7 Hz, 1H), 2.19-0.55 (m, 56H) ppm.

ESI-MS (m/z): $[M+Na]^+$ calculated for $C_{44}H_{72}ClNNaO_{11}{}^+$ 848.5; found 848.

Example 4

Preparation of C20-dehydroxy-C20-aminosalinomycin N-4-chlorobutyramide with the Formula (12)

(12)

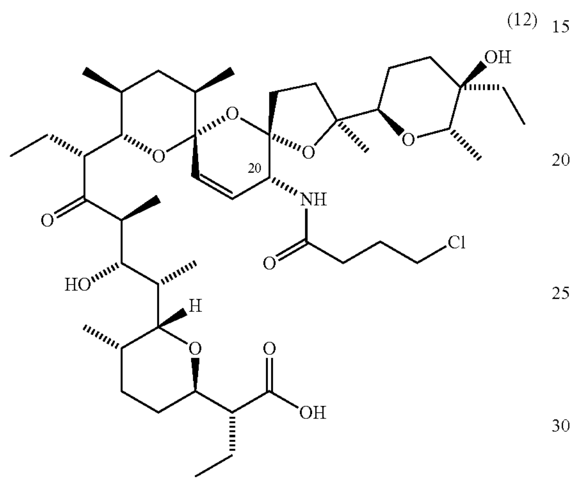

Proceeding as in example 1, except that instead of acetyl chloride (1.2 eq), 4-chlorobutyryl chloride (12 mg, 1.2 eq) was added to the reaction mixture. C20-dehydroxy-C20-aminosalinomycin N-4-chlorobutyramide with the formula (12) was obtained as a white amorphous solid with 29% yield.

Yield: 17 mg, 29%. Isolated as a white, amorphous solid; purity >95% by NMR and a single spot on TLC.

Rf: 0.59 in ethyl acetate/n-hexane 50%. Green spots in phosphomolybdic acid (PMA).

$^{13}C$ NMR (101 MHz, $CD_2Cl_2$) a 215.3, 177.6, 172.3, 130.0, 123.8, 106.1, 99.9, 88.9, 77.7, 76.3, 75.1, 74.0, 72.1, 71.2, 69.0, 56.2, 49.7, 49.4, 48.6, 45.3, 41.3, 38.9, 37.4, 36.5, 33.6, 33.1, 31.1, 31.0, 29.4, 28.7, 28.5, 26.6, 25.9, 23.0, 22.4, 20.4, 17.9, 16.7, 15.9, 15.1, 13.34, 13.26, 12.2, 11.4, 7.2, 6.5 ppm.

$^1H$ NMR (403 MHz, $CD_2Cl_2$) δ ~13.00 (s, very br, 1H), 6.97 (d, J=8.0 Hz, 1H), 6.09 (dd, J=10.6, 2.5 Hz, 1H), 5.81 (dd, J=10.7, 2.5 Hz, 1H), 4.43 (dt, J=8.0, 2.4 Hz, 1H), 4.08 (dd, J=10.0, 1.4 Hz, 1H), 3.93 (dd, J=10, 9, 5.5 Hz, 1H), 3.88-3.80 (m, 2H), 3.62-3.57 (m, 2H), 2.90 (td, J=10.5, 4.1 Hz, 1H), 2.73 (ddd, J=14.1, 9.9, 7.1 Hz, 1H), 2.59 (dd, J=11.1, 2.0 Hz, 1H), 2.35 (tdd, J=14.8, 13.0, 7.3 Hz, 2H), 2.19-0.53 (m, 60H) ppm.

ESI-MS (m/z): $[M+Na]^+$ calculated for $C_{46}H_{76}ClNNaO_{11}^+$ 876.5; found 876.

Example 5

Preparation of C20-dehydroxy-C20-aminosalinomycin N-methoxyacetamide with the Formula (13)

(13)

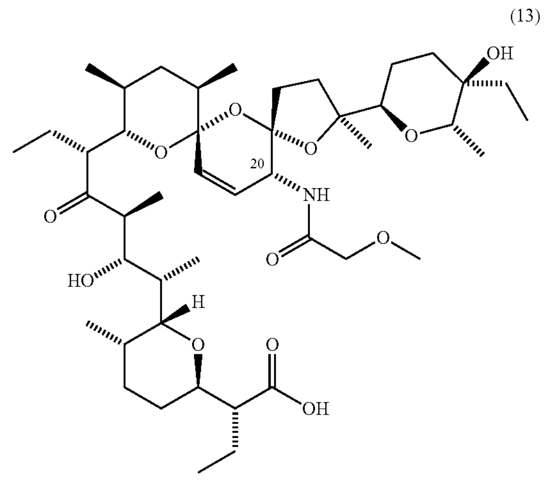

Proceeding as in example 1, except that instead of acetyl chloride (1.2 eq), methoxyacetyl chloride (9 mg, 1.2 eq) was added to the reaction mixture. C20-dehydroxy-C20-amino-salinomycin N-methoxyacetamide with the formula (13) was obtained as a white amorphous solid with 44% yield.

Yield: 24 mg, 44%. Isolated as a white, amorphous solid; purity >95% by NMR and a single spot on TLC.

Rf: 0.63 in ethyl acetate 100%. Green spots in phosphomolybdic acid (PMA).

$^{13}C$ NMR (101 MHz, $CDCl_3$) δ 215.5, 177.6, 169.8, 129.1, 123.2, 105.2, 99.5, 88.8, 77.2, 75.5, 74.8, 72.8, 72.3, 71.7, 71.0, 68.4, 58.9, 56.1, 49.8, 48.9, 48.2, 41.2, 38.7, 36.42, 36.38, 32.7, 30.6, 30.3, 29.2, 28.0, 26.2, 25.8, 22.7, 22.0, 19.9, 17.9, 16.5, 15.7, 14.3, 13.3, 12.9, 11.8, 11.0, 6.8, 6.4 ppm.

$^1H$ NMR (403 MHz, $CDCl_3$) δ ~13.00 (s, very br, 1H), 7.23 (d, J=8.9 Hz, 1H), 6.14 (dd, J=10.8, 2.9 Hz, 1H), 5.79 (dd, J=10.7, 1.7 Hz, 1H), 4.62 (ddd, J=8.9, 2.7, 1.9 Hz, 1H), 4.15 (dd, J=10.1, 1.4 Hz, 1H), 4.02-3.94 (m, 2H), 3.93-3.78 (m, 4H), 3.63 (dd, J=10.0, 1.9 Hz, 1H), 3.36 (s, J=9.3 Hz, 3H), 2.89 (td, J=10.9, 3.9 Hz, 1H), 2.74 (ddd, J=14.2, 10.0, 7.0 Hz, 1H), 2.61 (dd, J=10.9, 2.2 Hz, 1H), 2.22-0.60 (m, 56H) ppm.

ESI-MS (m/z): $[M+Na]^+$ calculated for $C45H75NNaO_{12}^+$ 844.5; found 844.

Example 6

Preparation of C20-dehydroxy-C20-aminosalinomycin N-1-adamantocarboxamide with the Formula (14)

(14)

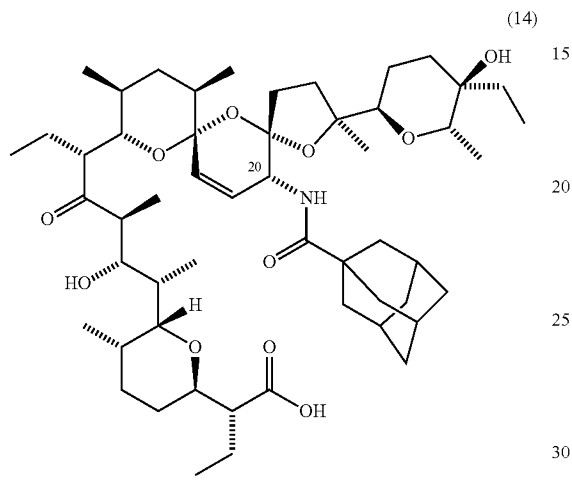

Proceeding as in example 1, except that instead of acetyl chloride (1.2 eq), 1-adamantocarbonyl chloride (17 mg, 1.2 eq) was added to the reaction mixture. C20-dehydroxy-C20-aminosalinomycin N-1-adamantocarboxamide with the formula (14) was obtained as a white amorphous solid with 12% yield.

Yield: 7 mg, 12%. Isolated as a white, amorphous solid; purity >95% by NMR and a single spot on TLC.

Rf: 0.52 in ethyl acetate/n-hexane 33%. Green spots in phosphomolybdic acid (PMA).

$^{13}$C NMR (101 MHz, $CD_2Cl_2$) δ 212.3, 179.2, 177.5, 132.7, 131.9, 109.2, 96.8, 86.0, 77.2, 74.9, 73.6, 72.5, 71.7, 71.0, 67.3, 53.4, 49.6, 49.2, 48.7, 40.9, 39.5, 39.19, 39.18, 36.7, 36.4, 35.6, 33.1, 32.6, 30.9, 30.1, 29.7, 28.5, 28.3, 26.4, 23.9, 23.5, 22.2, 20.2, 18.3, 17.8, 16.2, 14.6, 14.2, 13.3, 13.2, 12.2, 11.2, 7.3, 6.5 ppm.

$^{1}$H NMR (403 MHz, $CD_2Cl_2$) δ ~13.00 (s, very br, 1H), 6.40 (d, J=9.4 Hz, 1H), 5.86-5.71 (m, 2H), 4.75 (dt, J=9.3, 1.5 Hz, 1H), 4.22 (dd, J=9.8, 3.8 Hz, 1H), 3.92 (dd, J=10.9, 4.8 Hz, 1H), 3.79 (q, J=6.9 Hz, 1H), 3.64 (d, J=10.4 Hz, 1H), 3.60 (dd, J=10.0, 2.3 Hz, 1H), 3.48-3.40 (m, 1H), 2.93 (td, J=11.1, 3.6 Hz, 1H), 2.85 (d, J=5.0 Hz, 1H), 2.70-2.57 (m, 2H), 2.23 (ddd, J=13.3, 8.5, 6.9 Hz, 1H), 2.14-0.54 (m, 69H) ppm.

ESI-MS (m/z): $[M+Na]^+$ calculated for $C_{53}H_{85}NNaO_{11}{}^+$ 934.6; found 934.

Example 7

Preparation of C20-dehydroxy-C20-aminosalinomycin N-benzamide with the Formula (15)

(15)

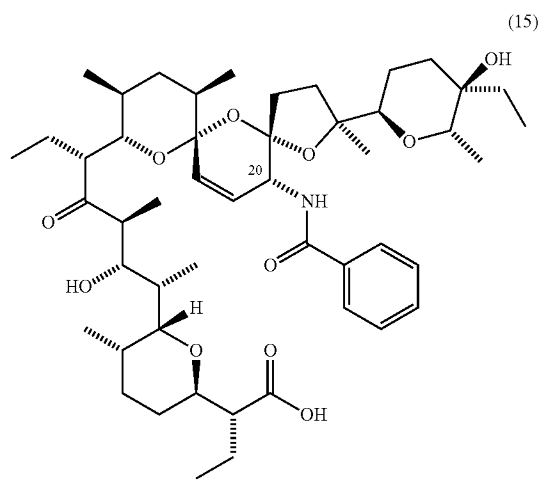

Proceeding as in example 1, except that instead of acetyl chloride (1.2 eq), benzoyl chloride (12 mg, 1.2 eq) was added to the reaction mixture. C20-dehydroxy-C20-aminosalinomycin N-benzamide with the formula (15) was obtained as a pale yellow amorphous solid with 91% yield.

Yield: 52 mg, 91%. Isolated as a pale yellow amorphous solid; purity >95% by NMR and a single spot on TLC.

Rf: 0.68 in ethyl acetate/n-hexane 50%. Green spots in phosphomolybdic acid (PMA), active under UV.

$^{13}$C NMR (101 MHz, $CD_2Cl_2$) δ 215.7, 177.6, 168.6, 136.0, 131.5, 129.8, 128.7, 127.5, 123.4, 105.9, 99.9, 89.3, 76.9, 76.3, 75.0, 73.4, 72.3, 71.1, 69.2, 56.3, 49.72, 49.66, 48.9, 41.6, 39.0, 37.2, 36.5, 33.2, 30.9, 30.7, 29.5, 28.6, 26.7, 26.1, 23.1, 22.6, 20.5, 18.0, 16.6, 15.9, 14.8, 13.4, 13.3, 12.0, 11.4, 7.2, 6.5 ppm.

$^{1}$H NMR (403 MHz, $CD_2Cl_2$) δ ~13.00 (s, very br, 1H), 7.75-7.67 (m, 2H), 7.50-7.44 (m, 1H), 7.43-7.36 (m, 2H), 7.19 (d, J=8.4 Hz, 1H), 6.14 (dd, J=10.7, 2.9 Hz, 1H), 5.88 (dd, J=10.7, 1.8 Hz, 1H), 4.68 (ddd, J=8.4, 2.7, 1.9 Hz, 1H), 4.10 (dd, J=10.1, 1.4 Hz, 1H), 3.97-3.87 (m, 2H), 3.85-3.79 (m, 1H), 3.59 (dd, J=10.0, 2.1 Hz, 1H), 3.28 (dd, J=13.6, 6.7 Hz, 1H), 2.88 (td, J=10.6, 4.0 Hz, 1H), 2.76 (dq, J=10.0, 7.1 Hz, 1H), 2.62 (dd, J=10.8, 2.0 Hz, 1H), 2.24-0.58 (m, 56H) ppm.

ESI-MS (m/z): $[M+Na]^+$ calculated for $C_{49}H_{75}NNaO_{11}{}^+$ 876.5; found 876.

Example 8

Preparation of C20-dehydroxy-C20-aminosalinomycin N-(4-chloromethyl)benzamide with the Formula (16)

(16)

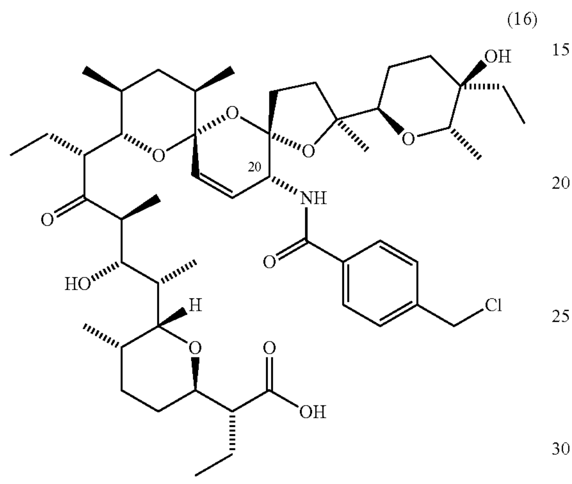

Proceeding as in example 1, except that instead of acetyl chloride (1.2 eq), 4-(chloromethyl)benzoyl chloride (16 mg, 1.2 eq) was added to the reaction mixture. C20-dehydroxy-C20-aminosalinomycin N-(4-chloromethyl)benzamide with the formula (16) was obtained as a white amorphous solid with 28% yield.

Yield: 17 mg, 28%. Isolated as a white, amorphous solid; purity >95% by NMR and a single spot on TLC.

Rf: 0.49 in ethyl acetate/n-hexane 33%. Green spots in phosphomolybdic acid (PMA), active under UV.

$^{13}C$ NMR (101 MHz, $CD_2Cl_2$) δ 214.8, 177.3, 167.9, 141.0, 135.8, 129.6, 128.9, 128.0, 123.4, 105.9, 99.7, 89.2, 76.8, 74.7, 73.5, 72.4, 71.2, 69.3, 56.2, 49.6, 49.2, 48.5, 45.9, 41.5, 38.8, 37.2, 36.2, 33.0, 30.87, 30.85, 30.0, 29.4, 28.8, 26.6, 26.1, 22.9, 22.4, 20.7, 17.8, 16.7, 15.8, 14.8, 13.4, 13.3, 12.0, 11.7, 7.5, 6.6 ppm.

$^{1}H$ NMR (403 MHz, $CD_2Cl_2$) δ ~13.00 (s, very br, 1H), 7.77-7.70 (m, 2H), 7.46-7.40 (m, 2H), 7.20 (d, J=8.4 Hz, 1H), 6.15 (dd, J=10.7, 2.8 Hz, 1H), 5.88 (dd, J=10.6, 1.8 Hz, 1H), 4.69 (ddd, J=8.3, 2.5, 2.1 Hz, 1H), 4.60 (s, J=9.2 Hz, 2H), 4.10 (dd, J=10.0, 1.3 Hz, 1H), 3.94 (ddd, J=10.9, 6.1, 1.7 Hz, 1H), 3.87 (d, J=10.2 Hz, 1H), 3.77 (dd, J=10.1, 3.1 Hz, 1H), 3.60 (dd, J=9.9, 2.1 Hz, 1H), 3.38 (dd, J=13.6, 6.8 Hz, 1H), 2.87 (td, J=10.3, 4.2 Hz, 1H), 2.78 (ddd, J=14.3, 9.8, 7.1 Hz, 1H), 2.62-2.56 (m, 1H), 2.24-0.54 (m, 56H) ppm.

ESI-MS (m/z): $[M+Na]^+$ calculated for $C_{50}H_{76}ClNNaO_{11}^+$ 924.5; found 924.

Example 9

Preparation of C20-dehydroxy-C20-aminosalinomycin N-2-furamide with the Formula (17)

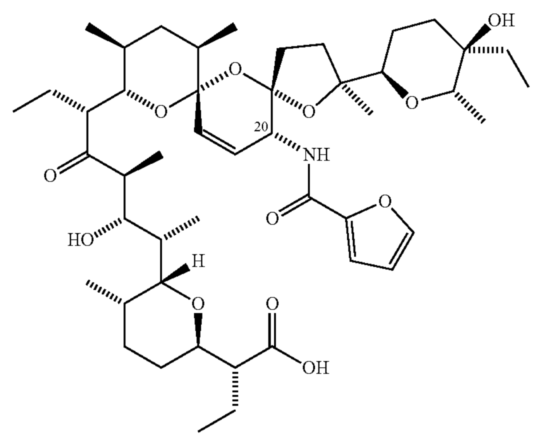

Proceeding as in example 1, except that instead of acetyl chloride (1.2 eq), 2-furoyl chloride (11 mg, 1.2 eq) was added to the reaction mixture. C20-dehydroxy-C20-aminosalinomycin N-2-furamide with the formula (17) was obtained as a white amorphous solid with 53% yield.

Yield: 30 mg, 53%. Isolated as a white, amorphous solid; purity >95% by NMR and a single spot on TLC.

Rf: 0.66 in ethyl acetate/n-hexane 50%. Green spots in phosphomolybdic acid (PMA), active under UV.

$^{13}C$ NMR (101 MHz, $CD_2Cl_2$) δ 219.6, 184.7, 158.8, 147.6, 145.5, 128.6, 123.7, 114.8, 111.9, 107.0, 100.0, 89.3, 77.4, 77.0, 76.6, 73.7, 71.5, 70.5, 69.1, 56.7, 51.1, 49.6, 48.2, 41.2, 39.3, 37.5, 36.2, 33.0, 32.7, 32.5, 28.7, 28.4, 27.3, 26.4, 23.5, 20.6, 20.4, 18.0, 16.3, 15.8, 14.5, 13.5, 12.7, 12.6, 11.4, 7.2, 7.0 ppm.

$^{1}H$ NMR (403 MHz, $CD_2Cl_2$) δ ~13.00 (s, very br, 1H), 7.52 (dd, J=1.7, 0.8 Hz, 1H), 7.37 (d, J=9.8 Hz, 1H), 7.27 (dd, J=3.5, 0.8 Hz, 1H), 6.42 (dd, J=3.5, 1.7 Hz, 1H), 6.18 (dd, J=10.8, 3.1 Hz, 1H), 5.75 (dd, J=10.8, 1.8 Hz, 1H), 4.95 (ddd, J=9.8, 3.0, 1.8 Hz, 1H), 4.14 (q, J=6.9 Hz, 1H), 4.08 (dd, J=10.4, 1.5 Hz, 1H), 3.94 (dd, J=10.8, 5.2 Hz, 1H), 3.71 (d, J=10.1 Hz, 1H), 3.66 (dd, J=10.3, 1.7 Hz, 1H), 3.44 (dd, J=12.3, 2.6 Hz, 1H), 2.74 (dddd, J=17.4, 13.6, 10.6, 4.4 Hz, 3H), 2.32-2.20 (m, 1H), 2.19-0.54 (m, 55H) ppm.

ESI-MS (m/z): $[M+Na]^+$ calculated for $C47H73NNaO_{12+}$ $_{866.5}$; found 866.

Example 10

Preparation of C20-dehydroxy-C20-aminosalinomycin N-methylcarbamate with the Formula (18)

(18)

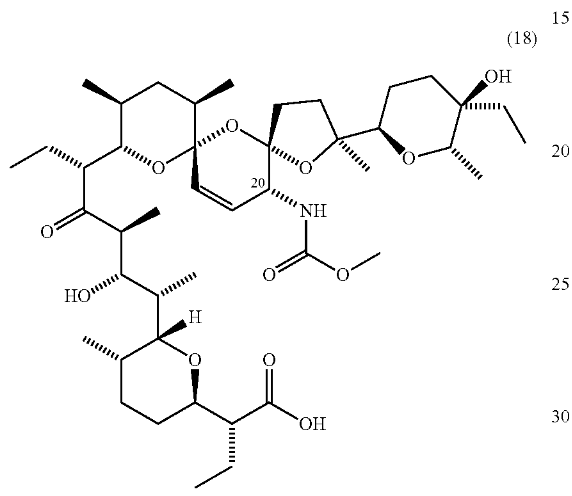

Proceeding as in example 1, except that instead of acetyl chloride (1.2 eq), methyl chloroformate (8 mg, 1.2 eq) was added to the reaction mixture. C20-dehydroxy-C20-aminosalinomycin N-methylcarbamate with the formula (18) was obtained as a white amorphous solid with 16% yield.

Yield: 9 mg, 16%. Isolated as a white, amorphous solid; purity >95% by NMR and a single spot on TLC.

Rf: 0.35 in ethyl acetate/n-hexane 50%. Green spots in phosphomolybdic acid (PMA).

$^{13}C$ NMR (101 MHz, $CD_2Cl_2$) δ 214.9, 177.2, 157.4, 130.1, 122.6, 105.8, 99.7, 89.6, 77.4, 76.4, 75.1, 74.4, 72.1, 71.2, 69.2, 56.5, 52.0, 50.7, 49.7, 48.4, 41.5, 38.9, 37.2, 36.5, 33.1, 31.0, 30.7, 29.4, 28.5, 26.7, 26.4, 23.1, 22.6, 20.3, 17.9, 16.8, 15.9, 14.4, 13.4, 13.3, 11.9, 11.3, 7.1, 6.5 ppm.

$^{1}H$ NMR (403 MHz, $CD_2Cl_2$) δ ~13.00 (s, very br, 1H), 6.39 (d, J=6.9 Hz, 1H), 6.04 (dd, J=10.8, 2.7 Hz, 1H), 5.83 (dd, J=10.7, 1.6 Hz, 1H), 4.12-4.04 (m, 2H), 3.99-3.85 (m, 3H), 3.81 (dd, J=13.7, 6.8 Hz, 1H), 3.66-3.53 (m, 4H), 2.91 (td, J=10.5, 4.2 Hz, 1H), 2.75 (ddd, J=14.2, 9.9, 7.1 Hz, 1H), 2.58 (dd, J=10.6, 1.4 Hz, 1H), 2.25-2.12 (m, 2H), 2.04-0.57 (m, 54H) ppm.

ESI-MS (m/z): $[M+Na]^+$ calculated for $C_{44}H_{73}NNaO_{12}^+$ 830.5; found 830.

Example 11

Preparation of C20-dehydroxy-C20-aminosalinomycin N-ethylcarbamate with the Formula (19)

(19)

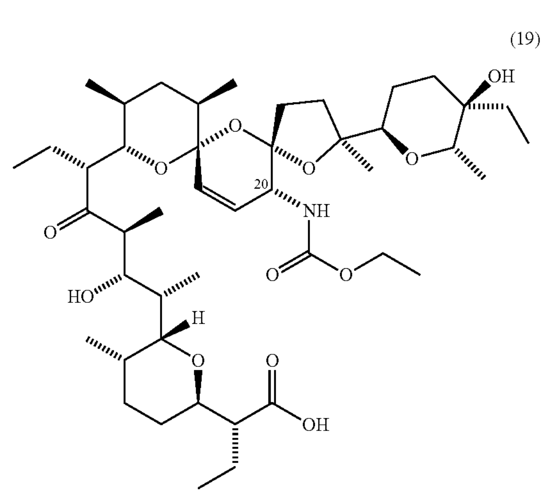

Proceeding as in example 1, except that instead of acetyl chloride (1.2 eq), ethyl chloroformate (9 mg, 1.2 eq) was added to the reaction mixture. C20-dehydroxy-C20-aminosalinomycin N-ethylcarbamate with the formula (19) was obtained as a white amorphous solid with 22% yield.

Yield: 12 mg, 22%. Isolated as a white, amorphous solid; purity >95% by NMR and a single spot on TLC.

Rf: 0.70 in ethyl acetate/n-hexane 50%. Green spots in phosphomolybdic acid (PMA).

$^{13}C$ NMR (101 MHz, $CDCl_3$) δ 215.3, 177.3, 156.7, 129.9, 122.0, 105.4, 99.4, 89.1, 77.2, 76.8, 75.7, 74.9, 73.8, 71.7, 71.0, 68.6, 60.5, 56.2, 50.4, 49.8, 48.5, 41.1, 38.6, 36.8, 36.3, 32.7, 30.6, 30.1, 29.3, 28.0, 26.3, 22.7, 22.3, 19.9, 17.9, 16.6, 15.7, 14.4, 14.1, 13.2, 12.9, 11.8, 11.0, 6.8, 6.3 ppm.

$^{1}H$ NMR (403 MHz, $CDCl_3$) δ ~13.00 (s, very br, 1H), 6.56 (d, J=7.2 Hz, 1H), 6.06 (dd, J=10.8, 2.7 Hz, 1H), 5.91 (dd, J=10.7, 1.5 Hz, 1H), 4.18-4.09 (m, 2H), 4.05 (q, J=7.1 Hz, 2H), 4.01-3.94 (m, 2H), 3.93-3.85 (m, 2H), 3.63 (dd, J=9.9, 1.8 Hz, 1H), 2.90 (td, J=10.9, 3.8 Hz, 1H), 2.75 (ddd, J=14.2, 9.9, 7.0 Hz, 1H), 2.59 (dd, J=10.8, 1.8 Hz, 1H), 2.27-2.12 (m, 2H), 2.10-0.50 (m, 57H) ppm.

ESI-MS (m/z): $[M+Na]^+$ calculated for $C_{45}H_{75}NNaO_{12}^+$ 844.5; found 844.

Example 12

Preparation of C20-dehydroxy-C20-aminosalinomycin N-neopentylcarbamate with the Formula (20)

(20)

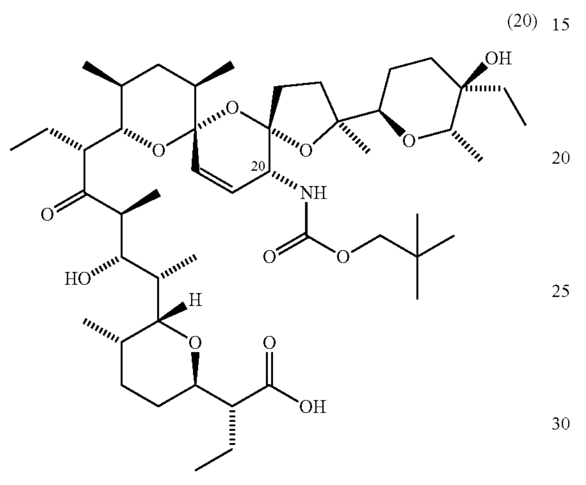

Proceeding as in example 1, except that instead of acetyl chloride (1.2 eq), neopentyl chloroformate (13 mg, 1.2 eq) was added to the reaction mixture. C20-dehydroxy-C20-aminosalinomycin N-neopentylcarbamate with the formula (20) was obtained as a white amorphous solid with 24% yield.

Yield: 14 mg, 24%. Isolated as a white, amorphous solid; purity >95% by NMR and a single spot on TLC.

Rf: 0.69 in ethyl acetate/n-hexane 50%. Green spots in phosphomolybdic acid (PMA).

$^{13}C$ NMR (101 MHz, $CD_2Cl_2$) δ 212.9, 177.8, 158.3, 134.1, 130.8, 109.3, 96.5, 86.7, 77.1, 75.0, 74.9, 74.2, 73.7, 71.8, 70.9, 67.3, 53.6, 51.3, 49.4, 49.0, 39.5, 36.74, 36.71, 36.3, 32.9, 31.6, 31.1, 30.7, 29.8, 28.3, 26.5, 26.4, 26.0, 23.3, 22.7, 20.2, 18.2, 17.2, 16.2, 14.8, 13.4, 13.2, 12.4, 11.1, 7.3, 6.5 ppm.

$^{1}H$ NMR (403 MHz, $CD_2Cl_2$) δ ~13.00 (s, very br, 1H), 6.90 (d, J=7.9 Hz, 1H), 5.87 (dd, J=9.7, 2.0 Hz, 1H), 5.74 (dd, J=9.7, 2.9 Hz, 1H), 4.30 (ddd, J=7.9, 2.7, 2.2 Hz, 1H), 4.18 (dd, J=10.0, 3.5 Hz, 1H), 3.96-3.87 (m, 3H), 3.69 (d, J=10.3 Hz, 1H), 3.61-3.51 (m, 3H), 2.93 (td, J=10.9, 3.7 Hz, 1H), 2.86 (d, J=4.8 Hz, 1H), 2.72-2.60 (m, 2H), 2.37 (s, 1H), 2.33-2.10 (m, 4H), 2.05-0.53 (m, 59H) ppm.

ESI-MS (m/z): $[M+Na]^+$ calculated for $C_{48}H_{81}NNaO_{12}^+$ 887.1; found 887.

Example 13

Preparation of C20-dehydroxy-C20-aminosalinomycin N-2,2,2-trichloroethylcarbamate with the Formula (21)

(21)

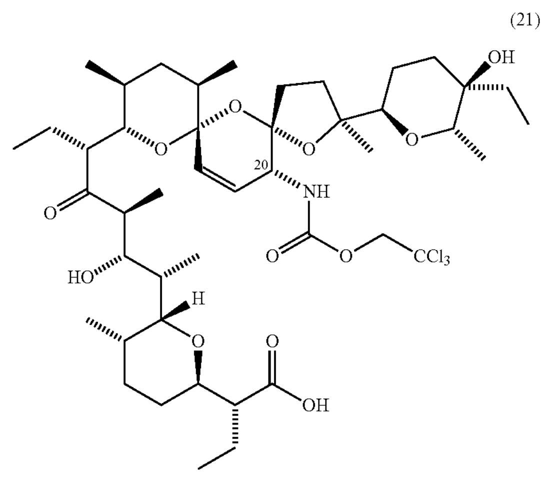

Proceeding as in example 1, except that instead of acetyl chloride (1.2 eq), 2,2,2-trichloroethyl chloroformate (18 mg, 1.2 eq) was added to the reaction mixture. C20-dehydroxy-C20-aminosalinomycin N-2,2,2-trichloroethylcarbamate with the formula (21) was obtained as a white amorphous solid with 41% yield.

Yield: 32 mg, 41%. Isolated as a white, amorphous solid; purity >95% by NMR and a single spot on TLC.

Rf: 0.50 in ethyl acetate/n-hexane 33%. Green spots in phosphomolybdic acid (PMA).

$^{13}C$ NMR (101 MHz, $CD_2Cl_2$) δ 216.6, 178.0, 155.2, 129.6, 123.2, 105.5, 100.2, 89.8, 77.7, 76.2, 75.4, 75.1, 74.4, 72.2, 71.4, 69.1, 56.6, 51.8, 50.2, 49.2, 49.1, 41.7, 39.2, 37.4, 36.9, 33.3, 31.4, 30.4, 29.8, 28.5, 26.8, 26.6, 23.3, 22.9, 20.3, 18.2, 17.0, 16.0, 14.9, 13.5, 13.4, 12.4, 11.3, 7.1, 6.9 ppm.

$^{1}H$ NMR (403 MHz, $CD_2Cl_2$) δ ~13.00 (s, very br, 1H), 7.01 (d, J=6.6 Hz, 1H), 6.09 (dd, J=10.8, 2.7 Hz, 1H), 5.88 (dd, J=10.7, 1.5 Hz, 1H), 4.70 (q, J=12.1 Hz, 2H), 4.11 (ddd, J=6.9, 2.6, 1.8 Hz, 1H), 4.07 (dd, J=10.2, 0.9 Hz, 1H), 3.99 (dt, J=8.7, 6.8 Hz, 3H), 3.94-3.86 (m, 3H), 3.57 (dd, J=10.0, 2.0 Hz, 1H), 2.89 (td, J=10.8, 4.1 Hz, 1H), 2.75 (dq, J=9.7, 7.1 Hz, 1H), 2.63 (dd, J=10.8, 2.0 Hz, 1H), 2.29-2.19 (m, 2H), 2.12-0.51 (m, 52H) ppm.

ESI-MS (m/z): $[M+Na]^+$ calculated for $C_{45}H_{72}Cl_3NNaO_{12}^+$ 948.4; found 948.

Example 14

Preparation of C20-dehydroxy-C20-aminosalinomycin N-propargylcarbamate with the Formula (22)

(22)

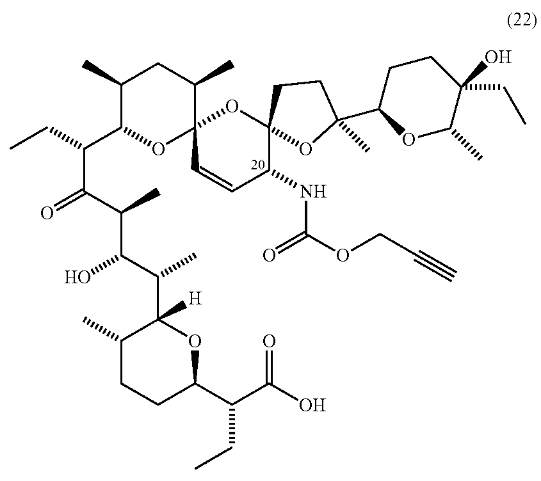

Proceeding as in example 1, except that instead of acetyl chloride (1.2 eq), propargyl chloroformate (10 mg, 1.2 eq) was added to the reaction mixture. C20-dehydroxy-C20-aminosalinomycin N-propargylcarbamate with the formula (22) was obtained as a white amorphous solid with 26% yield.

Yield: 14 mg, 26%. Isolated as a white, amorphous solid; purity >95% by NMR and a single spot on TLC.

Rf: 0.59 in ethyl acetate/n-hexane 50%. Green spots in phosphomolybdic acid (PMA).

$^{13}C$ NMR (101 MHz, $CD_2Cl_2$) δ 215.1, 177.3, 155.8, 129.7, 122.8, 105.7, 99.7, 89.7, 78.8, 77.3, 76.4, 75.1, 74.4, 74.3, 72.1, 71.3, 69.2, 56.5, 52.6, 50.9, 49.7, 48.5, 41.5, 38.9, 37.3, 36.5, 33.1, 31.1, 30.6, 29.5, 28.5, 26.7, 26.4, 23.1, 22.7, 20.3, 18.0, 16.8, 15.9, 14.6, 13.4, 13.3, 12.1, 11.3, 7.1, 6.5 ppm.

$^{1}H$ NMR (403 MHz, $CD_2Cl_2$) δ ~13.00 (s, very br, 1H), 6.68 (d, J=6.9 Hz, 1H), 6.05 (dd, J=10.8, 2.7 Hz, 1H), 5.83 (dd, J=10.7, 1.5 Hz, 1H), 4.64 (dd, J=15.6, 2.5 Hz, 1H), 4.54 (dd, J=15.6, 2.5 Hz, 1H), 4.08 (ddd, J=6.5, 3.3, 1.7 Hz, 2H), 4.00-3.83 (m, 4H), 3.58 (dd, J=10.0, 1.7 Hz, 1H), 2.91 (td, J=10.5, 4.2 Hz, 1H), 2.75 (ddd, J=14.1, 9.8, 7.1 Hz, 1H), 2.58 (dd, J=10.8, 1.5 Hz, 1H), 2.44 (t, J=2.4 Hz, 1H), 2.19 (tt, J=20.6, 10.3 Hz, 2H), 2.03-0.55 (m, 54H) ppm.

ESI-MS (m/z): $[M+Na]^+$ calculated for $C_{46}H_{73}NNaO_{12}^+$ 854.5; found 854.

Example 15

Preparation of propylurea of C20-dehydroxy-C20-aminosalinomycin with the Formula (23)

(23)

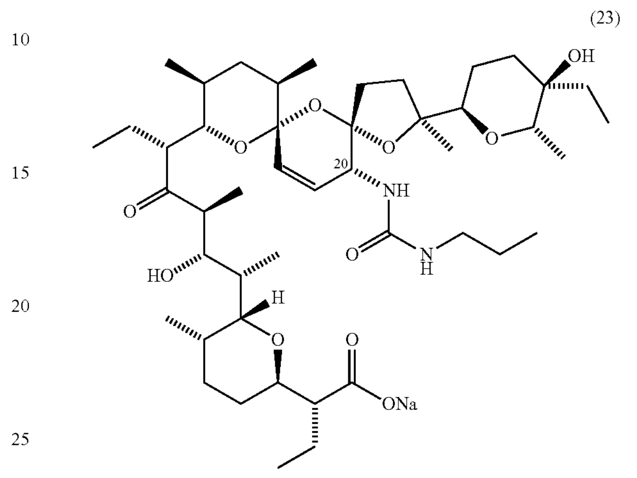

Propyl isocyanate (18 mg, 3.0 eq.) was added to a solution of C20-aminosalinomycin (50 mg, 1.0 eq.) in anhydrous methylene chloride (7 mL) at room temperature. This was stirred at room temperature until the reaction was over, which was monitored by thin-layer chromatography TLC.

Once the reaction was over, the reaction mixture was washed with an aqueous solution of sodium bicarbonate (0.1 M). The organic layer was evaporated until dry under reduced pressure and the residue was purified using a CombiFlash® chromatograph with ELS detector, using a silica-filled column and a solvent mixture of ethyl acetate: n-hexane with an increasing gradient of ethyl acetate concentration from 0% to 100%. The combined fractions containing propylurea of C20-dehydroxy-C20-aminosalinomycin with the formula (23) were evaporated until dry under reduced pressure, the residue was dissolved in methylene chloride and then extracted with an aqueous solution of sodium carbonate (0.1 M). The combined organic layers were evaporated again until dry under reduced pressure, and then repeatedly evaporated with n-pentane. Propylurea of C20-dehydroxy-C20-aminosalinomycin with the formula (23) was obtained as a white amorphous solid with 66% yield.

Yield: 38 mg, 66%. Isolated as a white, amorphous solid; purity >95% by NMR and a single spot on TLC.

Rf: 0.64 in ethyl acetate/n-hexane 50%. Green spots in phosphomolybdic acid (PMA).

$^{13}C$ NMR (101 MHz, $CD_2Cl_2$) δ 219.7, 185.0, 158.3, 130.3, 122.9, 107.2, 99.4, 88.9, 76.4, 76.3, 76.0, 74.4, 71.7, 71.4, 68.5, 56.7, 51.1, 50.3, 47.2, 42.5, 41.1, 39.2, 37.5, 36.4, 33.1, 33.0, 32.8, 30.3, 28.6, 28.3, 27.3, 24.13, 24.07, 20.5, 20.2, 17.8, 16.3, 16.1, 14.9, 13.4, 12.9, 12.5, 11.9, 11.1, 7.0, 6.8 ppm.

$^{1}H$ NMR (403 MHz, $CD_2Cl_2$) δ 6.06 (dd, J=10.9, 3.0 Hz, 1H), 5.78 (t, J=5.6 Hz, 1H), 5.68 (dd, J=10.8, 1.9 Hz, 1H), 5.60 (d, J=10.0 Hz, 1H), 5.55 (s, 1H), 4.88 (d, J=4.8 Hz, 1H). 4.61 (ddd, J=9.9, 2.9, 2.0 Hz, 1H), 4.31 (q, J=6.9 Hz, 1H), 4.07 (ddd, J=10.5, 4.7, 1.5 Hz, 1H), 3.81 (dd, J=11.0, 4.7 Hz, 1H), 3.64 (dd, J=10.1, 2.1 Hz, 1H), 3.60 (d, J=10.2 Hz, 1H), 3.47 (dd, J=12.4, 3.0 Hz, 1H), 3.05-2.97 (m, 2H), 2.82 (td, J=11.1, 3.4 Hz, 1H), 2.76-2.66 (m, 2H), 2.25-0.50 (m, 59H) ppm.

ESI-MS (m/z): $[M+H]^+$ calculated for $C_{46}H_{78}N_2NaO_{11}^+$ 857.6; found 857.

Example 16

Preparation of butylurea of C20-dehydroxy-C20-aminosalinomycin with the Formula (24)

(24)

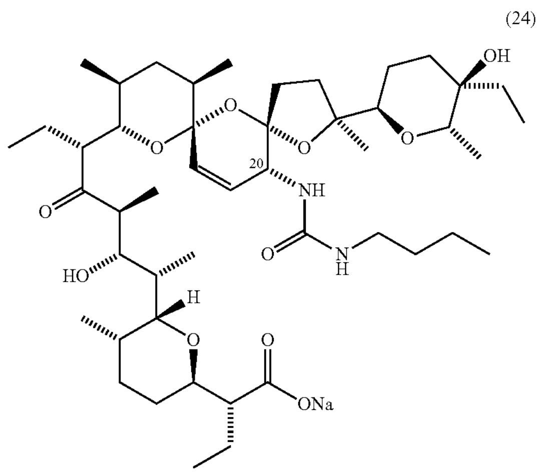

Proceeding as in example 15, except that instead of propyl isocyanate (3.0 eq), butyl isocyanate (21 mg, 3.0 eq) was added to the reaction mixture. Butylurea of C20-dehydroxy-C20-aminosalinomycin with the formula (24) was obtained as a white amorphous solid with 91% yield.

Yield: 53 mg, 91%. Isolated as a white, amorphous solid; purity >95% by NMR and a single spot on TLC.

Rf: 0.70 in ethyl acetate/n-hexane 50%. Green spots in phosphomolybdic acid (PMA).

$^{13}C$ NMR (101 MHz, $CD_2Cl_2$) δ 219.5, 184.9, 158.1, 129.9, 122.8, 106.9, 99.1, 88.7, 76.2, 75.8, 74.2, 71.5, 71.2, 68.2, 56.4, 50.8, 50.0, 47.0, 40.9, 40.4, 40.2, 38.9, 37.2, 36.2, 32.9, 32.8, 32.5, 28.3, 28.1, 28.0, 27.0, 23.9, 20.5, 20.4, 20.2, 20.0, 17.6, 16.1, 15.9, 14.7, 14.0, 13.2, 12.7, 12.3, 10.9, 6.8, 6.6 ppm.

$^1H$ NMR (403 MHz, $CD_2Cl_2$) δ 6.07 (dd, J=10.9, 3.0 Hz, 1H), 5.79 (t, J=5.5 Hz, 1H), 5.68 (dd, J=10.8, 1.9 Hz, 1H), 5.62 (d, J=10.0 Hz, 1H), 5.52 (s, J=10.6 Hz, 1H), 4.85 (d, J=4.7 Hz, 1H), 4.81-4.73 (m, 1H), 4.60 (ddd, J=9.9, 2.9, 2.0 Hz, 1H), 4.30 (q, J=6.8 Hz, 1H), 4.08 (ddd, J=10.5, 4.7, 1.5 Hz, 1H), 3.82 (dd, J=11.0, 4.7 Hz, 1H), 3.64 (dd, J=10.2, 2.1 Hz, 1H), 3.60 (d, J=10.1 Hz, 1H), 3.47 (dd, J=12.4, 2.9 Hz, 1H), 3.14-3.01 (m, 4H), 2.83 (td, J=11.1, 3.4 Hz, 1H), 2.71 (tt, J=6.9, 5.5 Hz, 2H), 2.25-0.50 (m, 58H) ppm.

ESI-MS (m/z): $[M+H]^+$ calculated for $C_{47}H_{80}N_2NaO_{11}^+$ 872.1; found 872.

Example 17

Preparation of 3-chloropropylurea of C20-dehydroxy-C20-aminosalinomycin with the Formula (25)

(25)

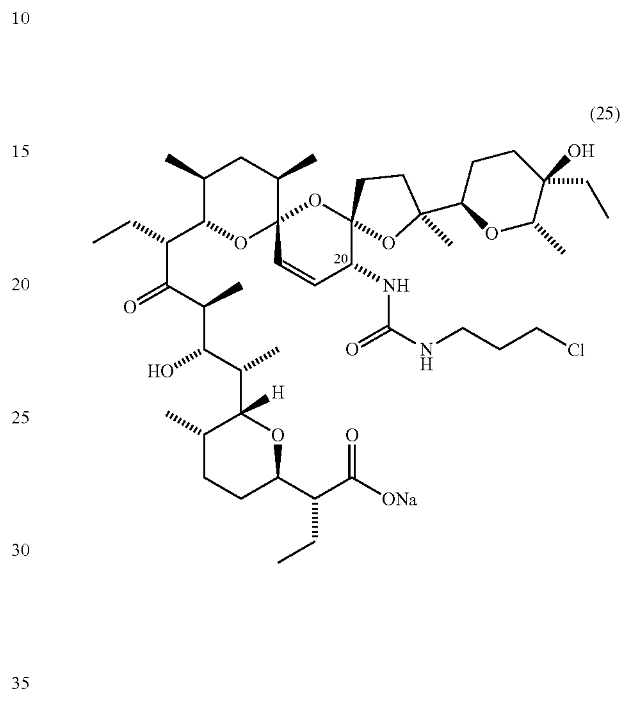

Proceeding as in example 15, except that instead of propyl isocyanate (3.0 eq), 3-chloropropyl isocyanate (25 mg, 3.0 eq) was added to the reaction mixture. 3-Chloropropylurea of C20-dehydroxy-C20-aminosalinomycin with the formula (25) was obtained as a white amorphous solid with 23% yield.

Yield: 14 mg, 23%. Isolated as a white, amorphous solid; purity >95% by NMR and a single spot on TLC.

Rf: 0.51 in ethyl acetate/n-hexane 50%. Green spots in phosphomolybdic acid (PMA).

$^{13}C$ NMR (101 MHz, $CD_2Cl_2$) δ 218.7, 184.2, 157.4, 129.0, 122.1, 106.2, 98.4, 88.0, 75.4, 75.3, 75.1, 73.5, 70.7, 70.6, 67.5, 55.7, 50.1, 49.2, 46.2, 42.5, 40.1, 38.2, 36.9, 36.6, 35.4, 33.2, 32.11, 32.07, 31.8, 27.6, 27.5, 27.3, 26.3, 23.1, 19.5, 19.3, 16.9, 15.4, 15.1, 13.9, 12.5, 12.0, 11.6, 10.2, 6.0, 5.9 ppm.

$^1H$ NMR (403 MHz, $CD_2Cl_2$) δ 6.06 (dd, J=10.9, 3.0 Hz, 1H), 5.92 (t, J=5.7 Hz, 1H), 5.72 (d, J=9.9 Hz, 1H), 5.66 (dd, J=10.8, 1.8 Hz, 1H), 5.58 (s, 1H), 4.79 (d, J=4.6 Hz, 1H), 4.60 (ddd, J=9.9, 2.8, 2.0 Hz, 1H), 4.30 (dd, J=13.6, 6.8 Hz, 1H), 4.07 (ddd, J=10.7, 4.5, 1.2 Hz, 1H), 3.81 (dd, J=11.0, 4.7 Hz, 1H), 3.62 (dd, J=10.2, 2.0 Hz, 1H), 3.60-3.49 (m, 2H), 3.46 (dd, J=12.3, 2.9 Hz, 1H), 3.18 (dtdd, J=20.0, 13.4, 6.5, 5.7 Hz, 2H), 2.82 (td, J=11.1, 3.3 Hz, 1H), 2.76-2.64 (m, 2H), 2.25-0.50 (m, 57H) ppm.

ESI-MS (m/z): $[M+H]^+$ calculated for $C_{46}H_{77}ClN_2NaO_{11}^+$ 891.5; found 891.

Example 18

Preparation of C20-aminosalinomycin with the Formula (3)

(3)

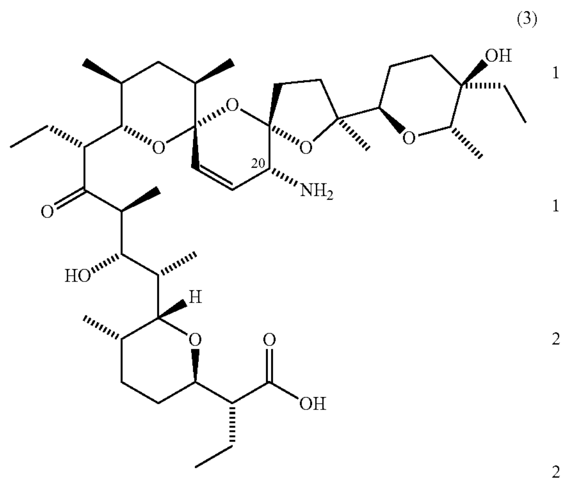

Excess of activated manganese(IV) oxide (231 mg, 20.0 eq.) was added portionwise to a solution of salinomycin (100 mg, 1.0 eq.) with the formula (1) in methylene chloride (15 mL) at room temperature. This was stirred at room temperature until the reaction was over, which was monitored by thin-layer chromatography TLC.

Once the reaction was over, the reaction mixture was filtered through a celite. The filtrate was then evaporated until dry under reduced pressure and the residue was purified using a CombiFlash® chromatograph with ELS detector, using a silica-filled column and a solvent mixture of ethyl acetate:n-hexane with an increasing gradient of ethyl acetate concentration from 0% to 50%. The combined organic layers comprising C20-oxosalinomycin with the formula (8) were evaporated again until dry under reduced pressure, and then repeatedly evaporated with n-pentane. C20-oxosalinomycin with the formula (8) was obtained as a white amorphous solid (96 mg, 96% yield).

In the next step, an ammonia solution (7.0 N in methanol, 0.7 mL) was added to the solution of C20-oxosalinomycin (90 mg, 1.0 eq.) with the formula (8) in methanol (7 mL) at room temperature. This was mixed at room temperature for 5 hours, followed by addition of $CeCl_3 \times 7H_2O$ (49 mg, 1.0 eq.), followed by, after 30 minutes, slow (overnight) addition of a solution of sodium cyanoborohydride—$NaBH_3CN$ (17 mg, 2.0 eq.) in methanol (5 mL). The progress of the reaction was monitored using thin layer chromatography TLC.

Once the reaction was over, the reaction mixture was evaporated until dry under reduced pressure and the residue was purified using a CombiFlash® chromatograph with ELS detector, using a silica-filled column and a solvent mixture of acetone:chloroform with an increasing gradient of acetone concentration from 0% to 60%. The combined organic layers comprising C20-aminosalinomycin with the formula (3) were evaporated again until dry under reduced pressure, and then repeatedly evaporated with n-pentane. C20-aminosalinomycin with the formula (3) was obtained as a white amorphous solid with 42% yield.

Yield: 38 mg, 42%. Isolated as a white, amorphous solid; purity >95% by NMR and a single spot on TLC.

Rf: 0.48 in acetone/methylene chloride 50%. Green spots in phosphomolybdic acid (PMA).

$^{13}C$ NMR (101 MHz, $CDCl_3$) δ 216.0, 182.4, 132.3, 128.7, 107.0, 99.7, 86.9, 77.5, 76.3, 75.8, 72.6, 71.8, 71.2, 67.9, 55.3, 51.5, 50.7, 48.2, 38.7, 37.5, 37.4, 36.5, 32.4, 31.3, 30.3, 29.5, 28.2, 26.9, 25.0, 24.1, 22.2, 20.6, 17.5, 16.5, 15.7, 15.1, 13.13, 13.09, 12.6, 11.2, 7.2, 6.6 ppm.

$^{1}H$ NMR (403 MHz, $CDCl_3$) δ 6.61-6.49 (m, 1H), 6.43 (d, J=9.3 Hz, 1H), 5.98 (d, J=46.8 Hz, 2H), 4.47 (d, J=9.0 Hz, 1H), 4.29 (d, J=62.7 Hz, 1H), 4.10 (d, J=6.0 Hz, 1H), 3.90 (dd, J=10.2, 3.1 Hz, 1H), 3.75 (d, J=9.5 Hz, 1H), 3.68-3.54 (m, 2H), 3.39 (d, J=28.4 Hz, 1H), 2.85-2.74 (m, 1H), 2.68-2.52 (m, 2H), 2.47-2.10 (m, 2H), 2.10-0.50 (m, 54H) ppm.

ESI-MS (m/z): $[M+H]^+$ calculated for $C_{42}H_{72}NO_{10}^+$ 750.5; found 750.

Example 19

Table 4 below summarises the test results for C20-epi-salinomycin derivatives versus corresponding derivatives according to the invention. The results presented clearly show that in neither case the epi derivatives show higher activity than the corresponding derivatives according to the invention. For some tested cell lines, salinomycin derivatives with the substituent at the C-20 position located at the epi position show a complete lack of activity thus presenting a difference of orders of magnitude compared to the derivatives according to the invention.

TABLE 3

Examples of use of compounds according to the invention.

| | Cancer cells | | | | | | | | | | | | | Normal cells |
|---|---|---|---|---|---|---|---|---|---|---|---|---|---|---|
| | B16-F0 | | Hs294T | | LoVo | | LoVo/DX | | | MCF-7 | | MV-4-11 | | BALB/3T3 |
| Test compound | $IC_{50}$ (μM) | SI | $IC_{50}$ (μM) | SI | $IC_{50}$ (μM) | SI | $IC_{50}$ (μM) | SI | RI | $IC_{50}$ (μM) | SI | $IC_{50}$ (μM) | SI | $IC_{50}$ (μM) |
| salinomycin (1) | 0.63 | 3.3 | 0.56 | 3.7 | 0.21 | 9.9 | 0.48 | 4.3 | 2.3 | 2.10 | 1.0 | 0.07 | 29.7 | 2.08 |
| (3) | 9.44 | 7.0 | 9.73 | 6.8 | 33.07 | 2.0 | 20.49 | 3.2 | 0.6 | 34.87 | 1.9 | 5.92 | 11.2 | 66.42 |
| (9) | 0.65 | 25.2 | 0.17 | 96.2 | 0.97 | 16.9 | 1.43 | 11.4 | 1.5 | 2.94 | 5.6 | 0.30 | 54.5 | 16.35 |
| (10) | 0.07 | 50.3 | 0.02 | 176.0 | 0.67 | 5.3 | 0.19 | 18.5 | 0.3 | 0.70 | 5.0 | 0.07 | 50.3 | 3.52 |
| (11) | 0.40 | 6.5 | 0.06 | 43.2 | 0.93 | 2.8 | 0.62 | 4.2 | 0.7 | 0.81 | 3.2 | 0.28 | 9.2 | 2.59 |
| (12) | 0.56 | 30.5 | 0.07 | 243.9 | 0.63 | 27.1 | 1.55 | 11.0 | 2.5 | 0.90 | 19.0 | 0.20 | 85.4 | 17.07 |
| (13) | 0.53 | 26.4 | 0.06 | 233.5 | 0.67 | 20.9 | 2.33 | 6.0 | 3.5 | 1.31 | 10.7 | 0.27 | 51.9 | 14.01 |
| (14) | 4.19 | 2.4 | 4.75 | 2.2 | 4.14 | 2.5 | 2.94 | 3.5 | 0.7 | 7.21 | 1.4 | 3.35 | 3.1 | 10.25 |
| (15) | 0.02 | 81.5 | 0.02 | 81.5 | 0.28 | 5.1 | 0.05 | 32.6 | 0.2 | 0.28 | 5.8 | 0.06 | 27.2 | 1.63 |

TABLE 3-continued

Examples of use of compounds according to the invention.

| | Cancer cells | | | | | | | | | | | | | Normal cells |
|---|---|---|---|---|---|---|---|---|---|---|---|---|---|---|
| | B16-F0 | | Hs294T | | LoVo | | LoVo/DX | | | MCF-7 | | MV-4-11 | | BALB/3T3 |
| Test compound | $IC_{50}$ (μM) | SI | $IC_{50}$ (μM) | SI | $IC_{50}$ (μM) | SI | $IC_{50}$ (μM) | SI | RI | $IC_{50}$ (μM) | SI | $IC_{50}$ (μM) | SI | $IC_{50}$ (μM) |
| (16) | 0.48 | 5.2 | 0.03 | 83.3 | 0.29 | 8.6 | 0.63 | 4.0 | 2.2 | 0.58 | 4.3 | 0.03 | 83.3 | 2.50 |
| (17) | 0.06 | 18.3 | 0.03 | 36.7 | 0.36 | 3.1 | 0.40 | 2.8 | 1.1 | 0.49 | 2.2 | 0.07 | 15.7 | 1.10 |
| (18) | 0.05 | 35.2 | 0.02 | 88.0 | 0.48 | 3.7 | 0.16 | 11.0 | 0.3 | 0.57 | 3.1 | 0.07 | 25.1 | 1.76 |
| (19) | 0.03 | 32.3 | 0.01 | 97.0 | 0.16 | 6.1 | 43.11 | 0.02 | 269.4 | 0.54 | 1.8 | 0.04 | 24.3 | 0.97 |
| (20) | 0.64 | 5.1 | 0.28 | 11.6 | 0.82 | 4.0 | 0.64 | 5.1 | 0.8 | 2.38 | 1.4 | 0.36 | 9.0 | 3.24 |
| (21) | 0.0034 | 197.1 | 0.0002 | 3350.0 | 0.09 | 7.4 | 0.05 | 13.4 | 0.6 | 0.36 | 1.9 | 0.02 | 33.5 | 0.67 |
| (22) | 0.02 | 66.0 | 0.0041 | 322.0 | 0.30 | 4.4 | 0.05 | 26.4 | 0.2 | 0.34 | 3.9 | 0.05 | 26.4 | 1.32 |
| (23) | 0.07 | 22.0 | 0.01 | 154.0 | 0.06 | 25.7 | 0.15 | 10.3 | 2.5 | 0.37 | 4.2 | 0.0011 | 1400.0 | 1.54 |
| (24) | 0.05 | 16.0 | 0.04 | 20.0 | 0.07 | 11.4 | 0.11 | 7.3 | 1.6 | 0.40 | 2.0 | 0.0010 | 800.0 | 0.80 |
| (25) | 0.01 | 135.0 | 0.0056 | 241.1 | 0.02 | 67.5 | 0.22 | 6.1 | 11.0 | 0.18 | 7.5 | 0.0003 | 4500.0 | 1.35 |
| cisplatin | 3.84 | 1.7 | 4.01 | 1.6 | 6.97 | 0.9 | 8.00 | 0.8 | 1.1 | 7.17 | 0.9 | 3.40 | 1.9 | 6.50 |

TABLE 4

| | Cancer cells | | | | | | | | | | | | | Normal cells |
|---|---|---|---|---|---|---|---|---|---|---|---|---|---|---|
| | B16-F0 | | Hs294T | | LoVo | | LoVo/DX | | | MCF-7 | | MV-4-11 | | BALB/3T3 |
| Test compound | $IC_{50}$ (μM) | SI | $IC_{50}$ (μM) | SI | $IC_{50}$ (μM) | SI | $IC_{50}$ (μM) | SI | RI | $IC_{50}$ (μM) | SI | $IC_{50}$ (μM) | SI | $IC_{50}$ (μM) |
| (10) | 0.07 | 50.3 | 0.02 | 176.0 | 0.67 | 5.3 | 0.19 | 18.5 | 0.3 | 0.70 | 5.0 | 0.07 | 50.3 | 3.52 |
| (10 epi) | | | 4.0 | 0.95 | | | | | | | | 0.4 | 9.5 | 3.8 |
| (12) | 0.56 | 30.5 | 0.07 | 243.9 | 0.63 | 27.1 | 1.55 | 11.0 | 2.5 | 0.90 | 19.0 | 0.20 | 85.4 | 17.07 |
| (12 epi) | | | NA | — | | | | | | | | 2.5 | 2.9 | 7.3 |
| (15) | 0.02 | 81.5 | 0.02 | 81.5 | 0.28 | 5.1 | 0.05 | 32.6 | 0.2 | 0.28 | 5.8 | 0.06 | 27.2 | 1.63 |
| (15 epi) | 0.4 | 2.5 | 0.08 | 12.5 | 0.2 | 5 | 0.63 | 1.6 | 3 | 1.1 | 0.9 | 0.033 | 30 | 1.0 |
| (19) | 0.03 | 32.3 | 0.01 | 97.0 | 0.16 | 6.1 | 43.11 | 0.02 | 269.4 | 0.54 | 1.8 | 0.04 | 24.3 | 0.97 |
| (19 epi) | 0.33 | 3 | 0.06 | 16 | 0.24 | 4.1 | 0.7 | 1.4 | 3 | 1.0 | 1 | 0.046 | 22 | 1 |
| (23) | 0.07 | 22.0 | 0.01 | 154.0 | 0.06 | 25.7 | 0.15 | 10.3 | 2.5 | 0.37 | 4.2 | 0.0011 | 1400.0 | 1.54 |
| (23 epi) | | | 3.8 | 1.5 | | | | | | | | 0.47 | 12.5 | 5.9 |
| (25) | 0.01 | 135.0 | 0.0056 | 241.1 | 0.02 | 67.5 | 0.22 | 6.1 | 11.0 | 0.18 | 7.5 | 0.0003 | 4500.0 | 1.35 |
| (25 epi) | | | 4.9 | 1.1 | | | | | | | | 0.6 | 9.3 | 5.6 |

NA—non-active

The invention claimed is:

1. A compound of a general formula (2)

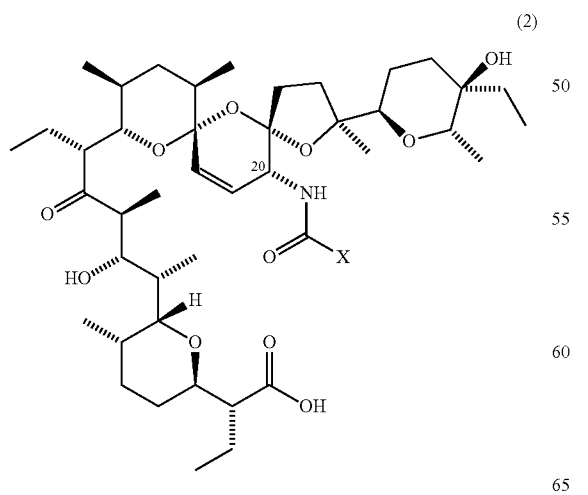

or a salt thereof;

wherein:

X is selected from R, O—R or NH—R;

wherein R is selected from:

a straight-chain or a branched-chain alkyl group comprising 1 to 10 carbons, a straight-chain or a branched-chain alkyl group comprising 1 to 10 carbons which is substituted at any carbon by 1 to 5 halogens, which may be present at the same carbon or at different carbons, a straight-chain alkyl group comprising 2 to 10 carbons which comprises ether moiety at any position of the straight-chain alkyl group, a straight-chain alkyl group comprising 3 to 10 carbons and comprising one or more double or triple bonds at any position of the straight-chain alkyl group, a monocyclic, dicyclic or tricyclic alkyl group comprising 5 to 10 carbons, an aryl group, an aryl group substituted by 1 to 3 substituents independently selected from alkyl, alkoxy, hydroxy, nitro, nitrile, and halogens, an heteroaryl group, wherein one or more carbons are substituted by 1 or more heteroatoms selected from oxygen, nitrogen, and sulphur, or an alkyl-aryl group, wherein the aryl group is optionally substituted by 1 to 3 substituents independently selected from alkyl, alkoxy, hydroxy, nitro, nitrile, and halogens and the alkyl group comprises 1 to 5 carbons.

2. The compound according to claim 1 selected from:

(9)

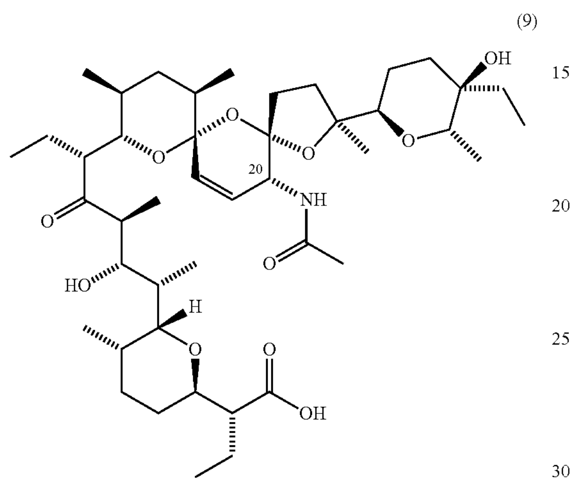

(10)

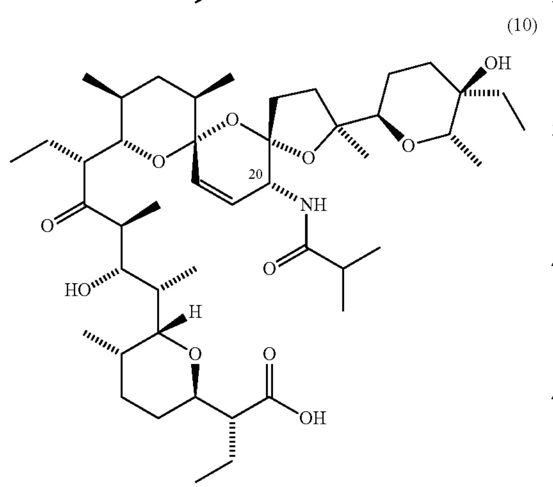

(11)

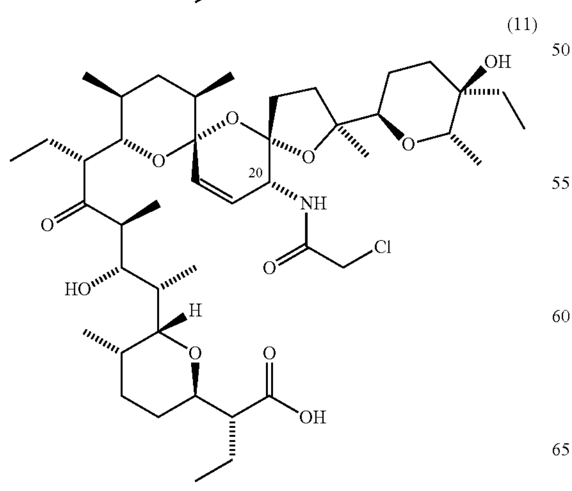

-continued (12)

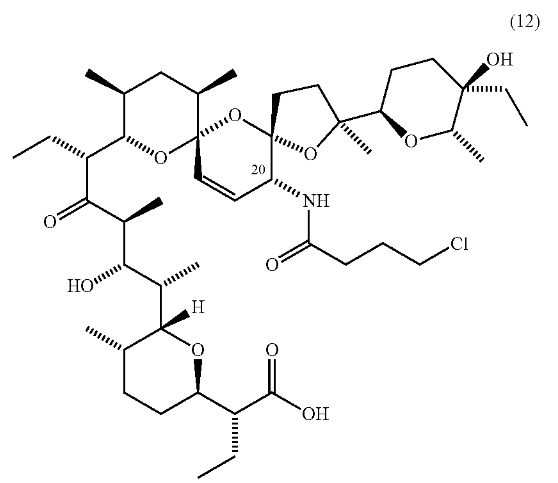

(13)

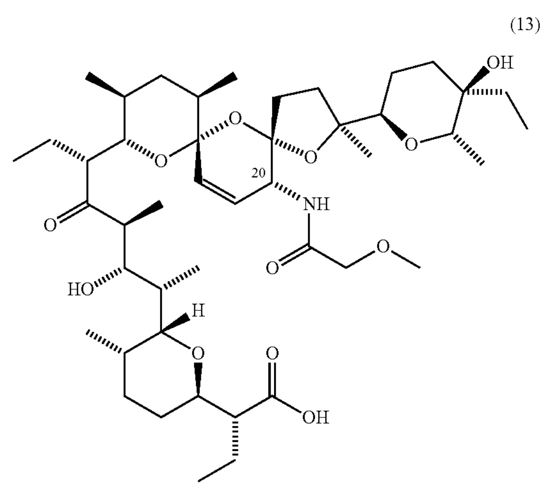

(14)

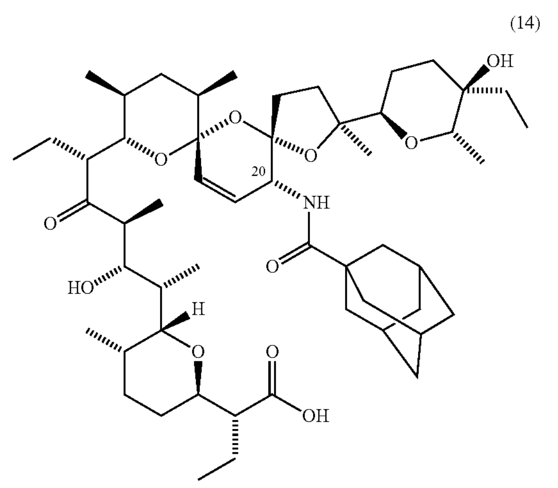

-continued
(15)
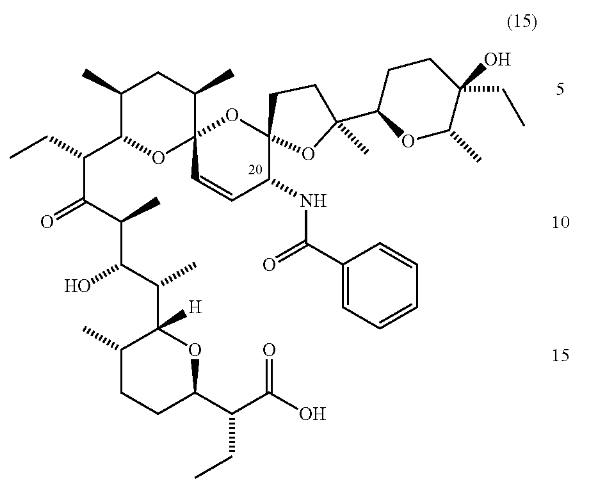
(16)
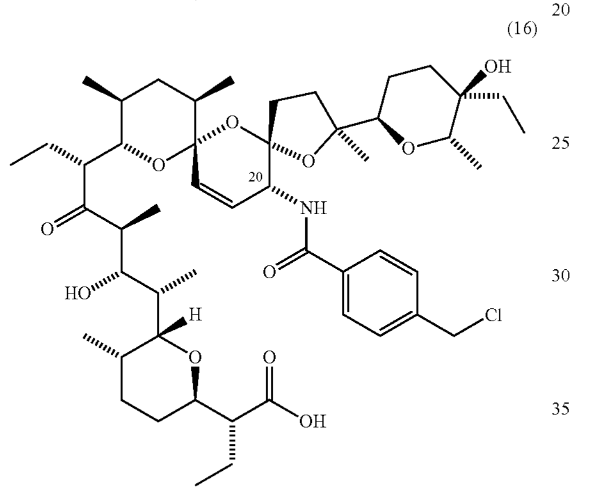
(17)
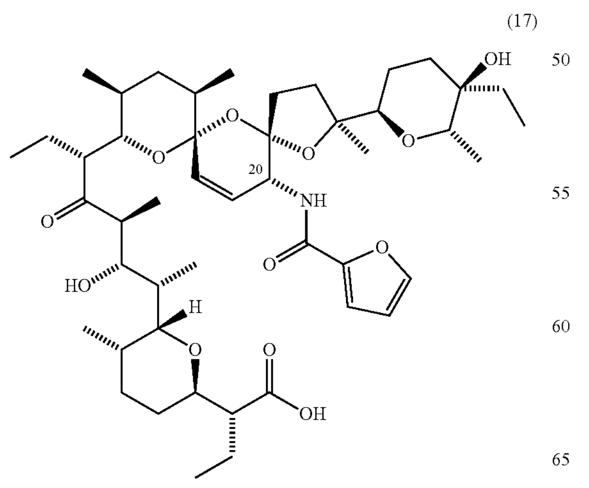
-continued
(18)
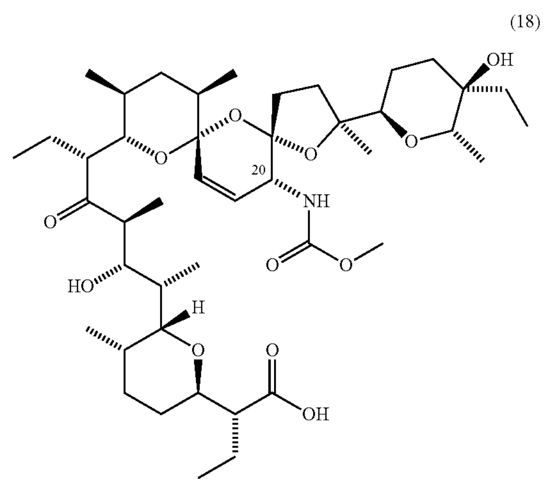
(19)
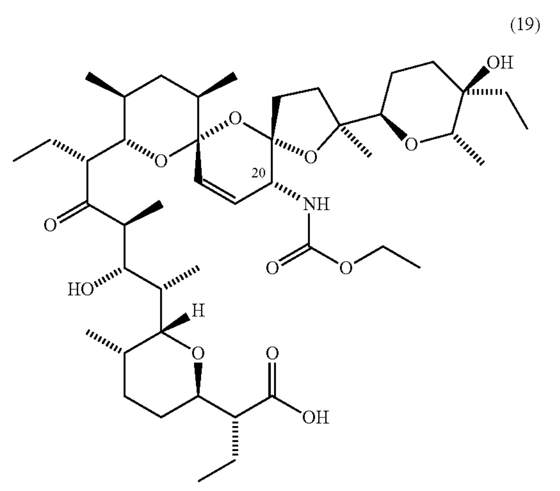
(20)
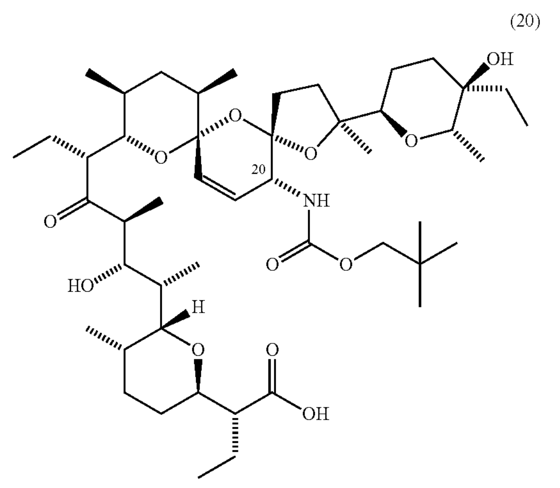

-continued
(21)
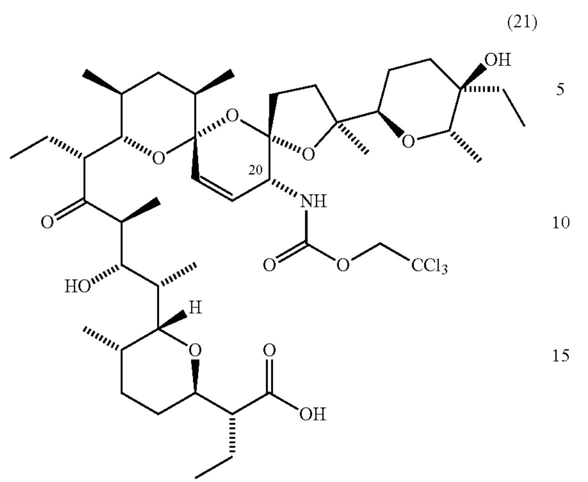
(22)
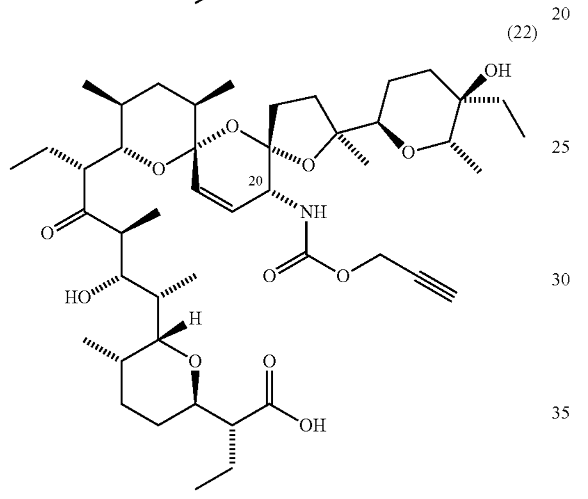
(23)
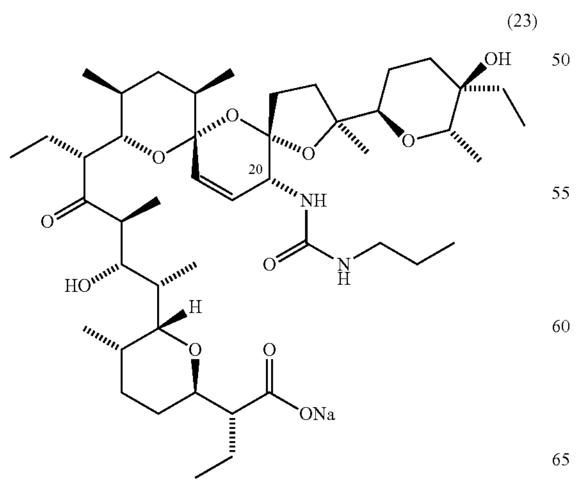
-continued
(24)
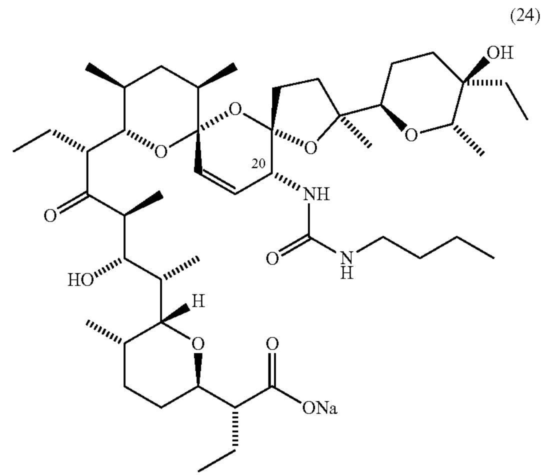
(25)
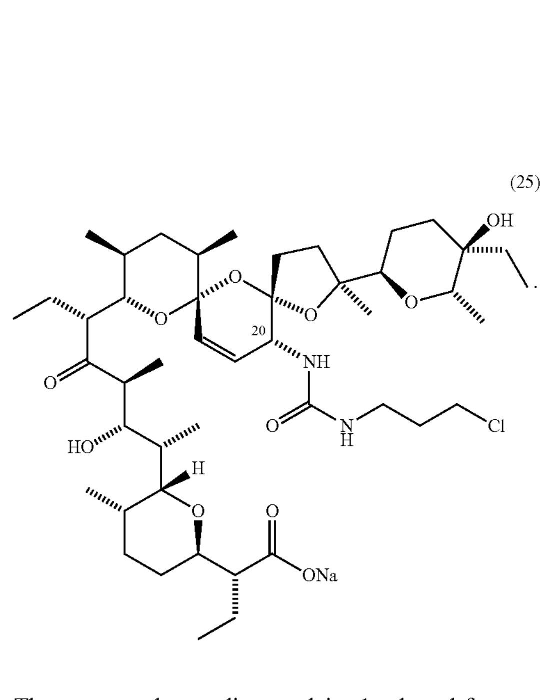
3. The compound according to claim 1 selected from:
(10)
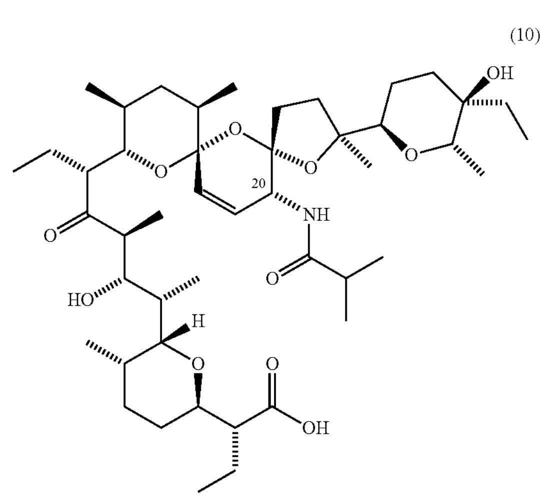

-continued
(12)
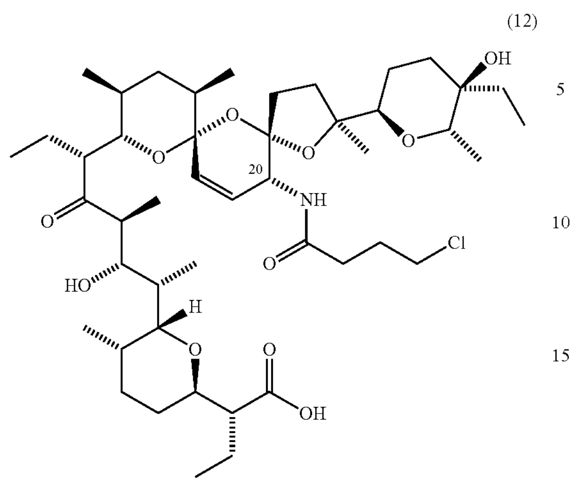
(13)
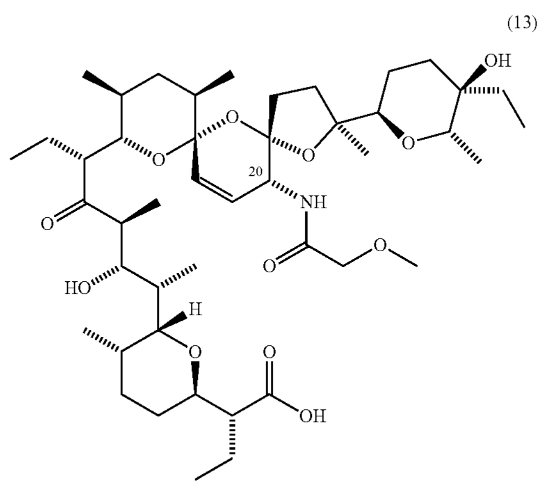
(21)
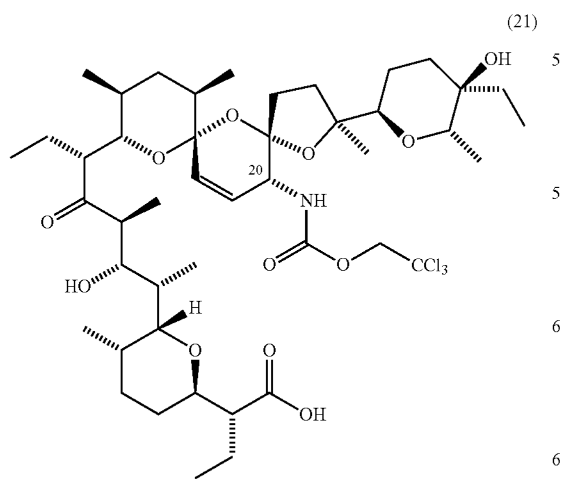
-continued
(22)
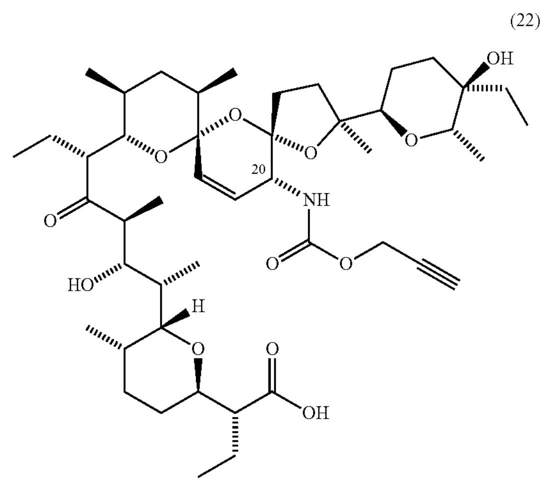
(23)
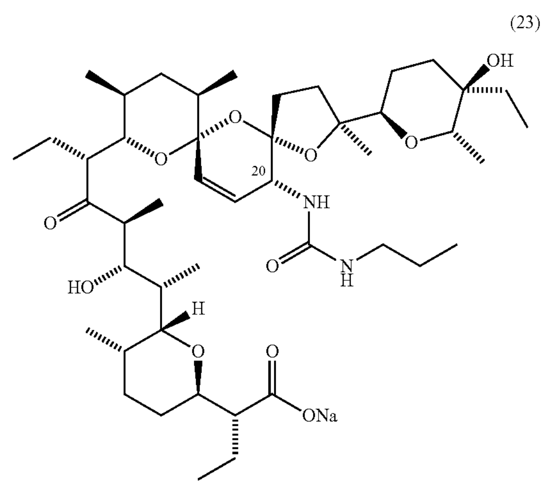
(25)
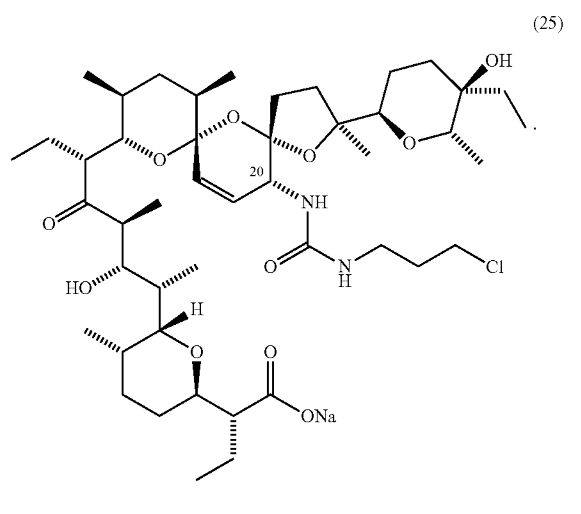

4. The compound according to claim 1 selected from:

(21)

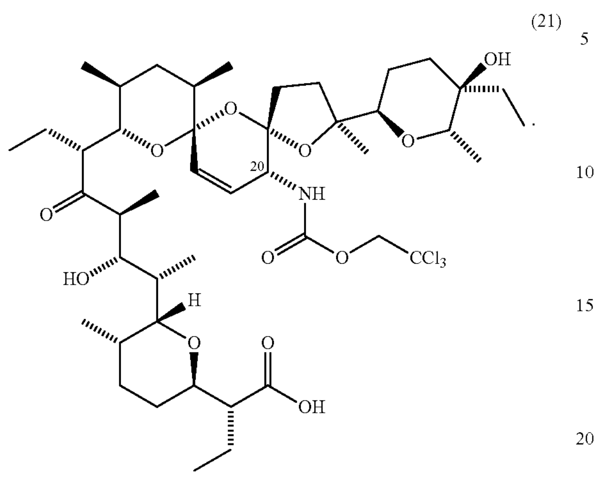

5. The compound according to claim 1, having the following formula:

(25)

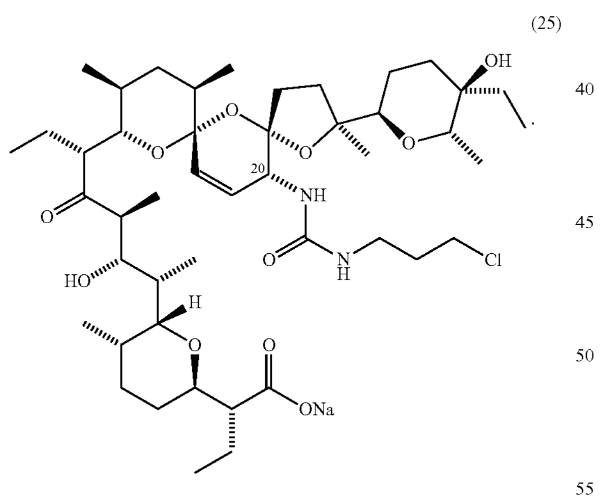

6. A pharmaceutical composition comprising the compound of claim 1 and at least one pharmaceutically acceptable excipient.

7. A method for obtaining the compound according to claim 1 comprising:

a) obtaining a compound of formula (3):

(3)

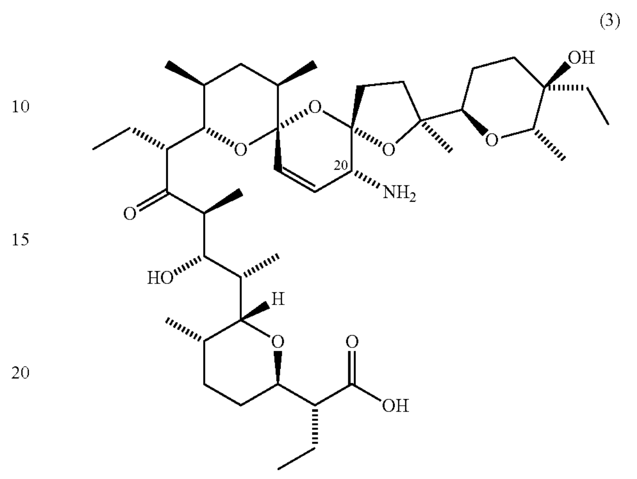

by stereoselective reductive amination of the compound of formula (8):

(8)

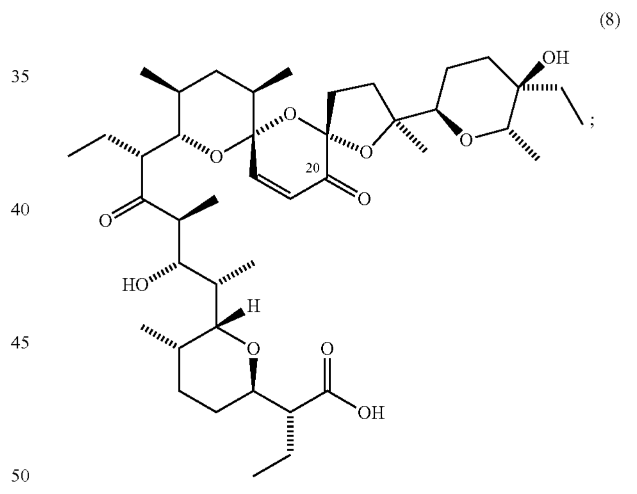

and b) reacting the compound of formula (3) and a compound selected from:

an acid chloride of general formula (4):

(4)

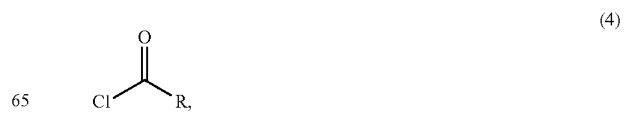

a carboxylic acid of general formula (5):

(5)

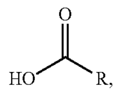

a chloroformate of general formula (6):

(6)

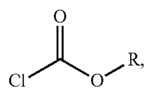

and an isocyanate with a of general formula (7):

(7)

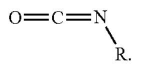

8. The method according to claim 7, further comprising: obtaining the compound of formula (8)

by a chemoselective oxidation reaction of a compound of formula (1):

(1)

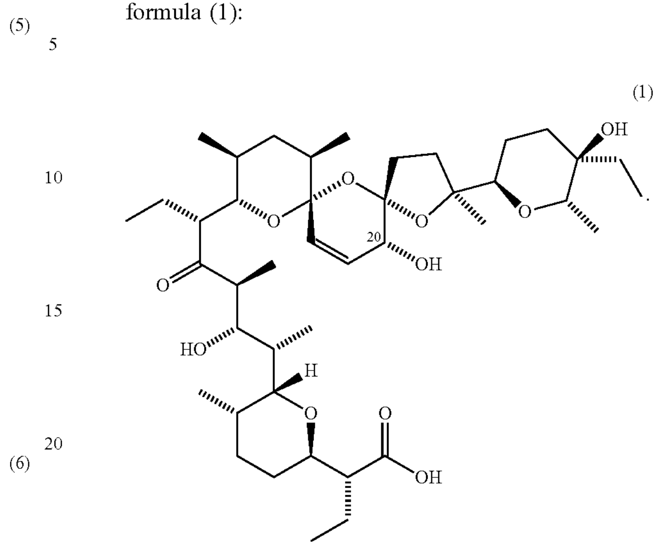

9. A method for treating cancer in a subject in need thereof comprising administering a compound according to claim 1.

10. The method according to claim 9 wherein the cancer is selected from leukaemia, non-small cell lung cancer, large intestine (colon) cancer, tumour of the central nervous system, melanoma, kidney cancer, prostate cancer, breast cancer, pancreatic cancer, sarcoma and uterine body cancer, drug-resistant sarcoma and uterine body cancer, cervical cancer, and bladder cancer.

11. The method according to claim 9 wherein the cancer is selected from the group comprising melanoma, colon cancer, breast cancer, and biphenotypic leukaemia.

12. The method according to claim 7, further comprising a step of transforming the resulting compound of step b) in acidic form into a salt of the compound of general formula (2).

* * * * *